US006033665A

United States Patent [19]
Yednock

[11] Patent Number: 6,033,665
[45] Date of Patent: *Mar. 7, 2000

[54] COMPOSITIONS AND METHODS FOR MODULATING LEUKOCYTE ADHESION TO BRAIN ENDOTHELIAL CELLS

[75] Inventor: Theodore A. Yednock, Fairfax, Calif.

[73] Assignee: Elan Pharmaceuticals, Inc., South San Francisco, Calif.

[*] Notice: This patent is subject to a terminal disclaimer.

[21] Appl. No.: 08/457,847

[22] Filed: Jun. 1, 1995

Related U.S. Application Data

[63] Continuation of application No. 08/402,962, Mar. 10, 1995, which is a continuation of application No. 07/871,223, Apr. 17, 1992, abandoned, which is a continuation-in-part of application No. 07/577,650, Sep. 4, 1990, Pat. No. 5,260, 210, which is a continuation-in-part of application No. 07/413,274, Sep. 27, 1989, abandoned.

[51] Int. Cl.$^7$ .......................... A61K 38/00; A61K 39/395
[52] U.S. Cl. ...................... 424/130.1; 424/141.1; 424/143.1; 424/144.1; 514/2; 530/300; 530/350; 530/387.1; 530/388.22; 530/389.1; 530/395
[58] Field of Search .................. 424/145.1, 158.1, 424/141.1, 143.1, 144.1, 130.1; 530/387.1, 388.82, 395, 300, 350, 388.22, 389.1; 935/107, 110; 514/2

[56] References Cited

U.S. PATENT DOCUMENTS

| | | |
|---|---|---|
| 4,208,406 | 6/1980 | Lapinet et al. . |
| 4,764,504 | 8/1988 | Johnson et al. . |
| 4,840,793 | 6/1989 | Todd et al. . |
| 5,272,263 | 12/1993 | Hession et al. ........................ 536/73.5 |
| 5,367,056 | 11/1994 | Hession et al. ......................... 530/380 |
| 5,730,978 | 3/1998 | Wayner ................................ 424/144.1 |

FOREIGN PATENT DOCUMENTS

| | | |
|---|---|---|
| 0 330 506 A2 | 2/1989 | European Pat. Off. . |
| WO 90/13300 | 11/1990 | WIPO . |
| WO 91/03252 | 3/1991 | WIPO . |
| WO 91/04745 | 4/1991 | WIPO . |
| WO 92/00751 | 1/1992 | WIPO . |

OTHER PUBLICATIONS

Greenwood et al, Immunology vol. 86 p. 408, 1995.
Audus, K.L. and Borchardt, R.T., "Characterization of an In Vitro Blood–Brain Barrier Model System for Studying Drug Transport and Metabolism", *Pharmaceutical Research*, 3:81–87 (1986).
Arthur et al., "Astrocyte–mediated induction of tight junctions in brain capillary endothelium: an efficient in vitro model", *Developmental Brain Research*, 36:155–159 (1987).
Carlos et al., "Vascular Cell Adhesion Molecule–1 Mediates Lymphocyte Adherence to Cytokine–Activated Cultured Human Endothelial Cells", *Blood*, 76(5)965–970 (1990).
Clayberger et al., "Identification and Charaterization of Two Novel Lymphocyte Function–Associated Antigens, L24 and L25[1]", *J. Immunol.*, 138:1510–1514 (1987).
Cybulsky, M.I. and Gimbrone, Jr., M.A., "Endothelial Expression of a Mononuclear Leukocyte Adhesion Molecule During Atherogenesis", *Science*, 251:788–791 (1991).
Duffey et al., "Regulation of epithelial tight junction permeability by cyclic AMP", *Nature*, 294:451–453 (1981).
Elices et al., "VCAM–1 on Activated Endothelium Interacts with the Leukocyte Integrin VLA–4 at a Site Distinct from the VLA–4/Fibronectin Binding Site", *Cell*, 60:577–584 (1990).
Freedman et al., "Adhesion of Human B Cells to Germinal Centers in Vitro Involves VLA–4 and INCAM–110", *Science*, 249:1030–1033 (1990).
Gudewicz et al., "A role for Anti–Inflammatory Agents and Cyclic AMP in Regulating Fibronectin–Mediated Phagocytosis", *J. Immunopharmacology*, 3(2):193–204 (1981).
Gumbiner et al., "The Role of the Cell Adhesion Molecule Uvomorulin inThe Formation and Maintenance of the Epithelial Junctinal Complex", *The Journal of Cell Biology*, 107:1575–1577 (1988).
Hemler, M.E., "Adhesive Protein Receptors on Hematopoietic Cells", *Immunology Today*, 9:109–113 (1988).
Hemler etr al., "Structure of the Integrin VLA–4 and its Cell–Cell and Cell–Matrix Adhesion Functions", *Immunol. Rev.*, 114:49–65 (1990).
Hemler et al., "Characterizaiton of the Cell surface Heterodimer VLA–4 and Related Peptides", *The Jouranl fo Biological Chemistry*, 262:11478–11485 (1987).
Holzmann et al., "Identification of a Murine Peyer's Patch–Specific Lymphocyte Homing Receptor as an Intergrin Molecule with an α Chain Homologous to Human VLA–4α", *Cell*, 56:37–46 (1989).
Janzer, R.C. and Raff, M.C., "Astrocytes Induce Blood–Brain Barrier Properties in Endothelial Cells", *Nature*, 325:253–257 (1987).
Killackey et al., "Increased Permeability of Microcarrier–Cultured Endothelial Monolayers in Response to Histamine and Thrombin", *Am. J. Pathol.*, 122(1):5061 (1986).
Kruse, P.F. and Paterson, Jr., M.K., "Microcarrier Cultures of Animal Cells", *Tissue Culture: Methods and Applications*, Chapter 2:372–377 (1973).
Leeson et al., *Histology*, W.B. Saunders Co., Philadelphia, pp. 251–253 (1976).

(List continued on next page.)

Primary Examiner—Paula K. Hutzell
Assistant Examiner—Nancy A. Johnson
Attorney, Agent, or Firm—Townsend & Townsend & Crew

[57] ABSTRACT

The invention is directed to compositions and methods for modulating the adhesion of leukocytes to brain endothelial cells. More specifically, the present invention relates to the use of reagents to inhibit the binding of VLA–4 leukocyte cell surface receptors to brain endothelial adhesion molecules. Also provided are compositions and methods for treating brain inflammation. A method of inducing brain inflammation as well as an assay for testing anti-inflammatory agents is also provided.

13 Claims, 9 Drawing Sheets

OTHER PUBLICATIONS

Machi et al., "Isolation and Characterization of Endothelial Cells From Bovine Cerebral Arteries", *In Vitro Cell*, 26:291–300 (1990).

Meyer et al., "A Derivative of Staurosporine (CGP 41 251) Shows Selectiveity for Protein Kinase C Inhibition and In Vitro Anti–Proliferative as Well as In Vivo Anti–Tumor Activity", *Int. J. Cancer*, 43:851–856 (1989).

Nemecek, G.M., "Properties of Adenylate Cyclase and Cyclic Nucleotide Phosphodiesterase in Hamster Isolated Capillary Preparations", *Biochimica et Biophysica Acta*, 628:125–135 (1980).

Osborn et al., "Direct Expression Cloning of Vascular Cell Adhesion Molecule 1, a Cytokine–Induced Endothelial Protein that Binds to Lymphocytes", *Cell*, 59:1203–1211 (1989).

Pierschbacher, M.D and Ruoslahti, E., "Variants of the Cell Recognition Site of Bibronectin that Retain Attachment–promoting Activity", *Proc. Natl. Acad. Sci. USA*, 81:5985–5988 (1984).

Pitzalis et al., "The Preferential Accumulationof Helper–Inducer T Lymphocytes in Inflammatory Lesions: Evidence for Regultion by Selective Endothelial and Homotypic Adhesion", *Eur. J. Immunol.*, 18:1397–1404 (1988).

Polte et al., Full Length Vascular Cell Adhesion Molecule 1 (VCAM–1), N.A.R. 18(19):5901 (1990).

Rice, G.E. and Bevilacqua, M.P., "An Inducible Endothelial Cell Surface Glycoprotein Mediates Melanoma Adhesion" *Science*, 246:1303–1033 (1989).

Sanchez–Madrid et al., "VLA–3: A Novel Polypeptide Assocation within the VLA molecular complex: Cell Distribution and Biochemical Characterization", *Eur. J. Immunol.*, 16:1343–1349 (1986).

Schwartz, B.R., "Identification of Surface Proteins Mediating Adherence of CD11/DC18–Deficient Lymphoblastoid Cells to Cultured Human Endothelium" *Immuno Chemistry*, 113:57012M, pp. 57018 (1990).

Shimizu et al., "Four Molecular Pathways to T Cell Adhesion Endothelial Cells: Roles of LFA–1, VCAM–1, as Changes in Pathway Hierarchy Under Different Activation Conditions", *The Journal of Cell Biology*, 113:1203–1212 (1991).

Springer, T.A., "Adhesion Receptors of the Immune System", *Nature*, 346:425–434 (1990).

Staquet et al., "A Surface Glycoprotein Complex Related to the Adhesive Receptors of the VLA Family, Shared by Epidermal Langerhans Cells and Basal Keratinocytes", *J. Invest. Derm.*, 92(5):739–745 (1989).

Takada et al., "The Primary Structure of the $\alpha^4$ subunit of VLA–4: Homology to Other Integrins and a Possible Cell–Cell Adhesion Function", *The EMBO Journal*, 8(5):1361–1368 (1989).

Tuomanen et al., "Reduction of Inflammation, Tissue Damage, and Mortality in Bacterial Meningitis in Rabbits Treated with Monoclonal Antibodies Against Adhesion–Promoting Receptors of Leukocytes", *J. Exp. Med.*, 170:9590968 (1989).

van Bree et al., "Carrier–Mediated Transport of Baclofen Across Monolayers of Bovine Brian Endothelial Cells in Primary Culture", *Pharmaceutical Research*, 5(6):369–371 (1988).

Yednock, T.A., "VLA–4 is Involved in Lymphocyte Binding to Brain Endothelium in Experimental Autoimmune Encephalitis", *Workshop on Adhesion Receptors in the Immune System*, pp. 65, Jun. 10, 1991.

Yednock et al., Prevention of Experimental Autoimmune Encephalomyelitis by Antibodies Against $\alpha 4\beta 1$ Integri, *Nature*, 356:63–66 (1992).

Audus et al., *Ann. N. Y. Acad. Sci.,* 507:9 (1987).

Behrens et al., "Dissociation of madin–darby canine kidney epithelial cells by the monoclonal antibody anti–arc–1: mechanistic aspects and identificationo f the antigen as a component related to uvomorulin," *J. Cell Biol.*, 101:1307–1315 (1985).

Birch et al., *Life Sciences*, 42(14):1355–1360 (1988).

*Chemical Abstracts*, 105(5):35047 (Aug. 4, 1986), Audus et al., "Characterization of an in vitro blood–brain barrier model system for studying drug transport and metabolism," see page 10, col. 1, *Pharm. Res.*, 3(2):81–87 (1986).

*Chemical Abstracts*, 96(13):97339k (Mar. 29, 1982), Gudewicz et al., "A role for antiinflammatory agents and cyclic amp in regulating fibronectin–mediated phagocytosis," *J. Immunopharmacol.*, 3(2):193–204 (1981).

*Chemical Abstracts*, 113(1):2864K (Jul. 2, 1990), Machi et al., "Isolation and characterizatgion of endothelial cells from bovine cerebral arteries," *In Vitro Cell. Dev. Biol.*, 26(3, 1):291–300 (1990).

*Chemical Abstracts*, 92(19):159462y (May 12, 1980), Nemecek, "Properties of adenylate cyclase and cyclic nucleotide phosphodiesterase in hamster isolated capillary preparations," *Biochem. & Biochim. Biophys. Acta*, 628(2):125–135 (1980).

*Chemical Abstracts,* 113(7):57012m (Aug. 13, 1990), Swartz et al., "Identification of surface proteins mediating adherence of cd11/cd18–deficient lymphoblastoid cells to cultured human endothelium," see page 511, cols. 1 and 2, *J. Clin. Invest.*, 85(6):2019–2022 (1990).

*Chemical Abstracts*, 109(9):66314f (Aug. 29, 1988), Van Bree et al., "Carrier–mediated transport of bovine brain endothelial cells in primary culture," see page 12, col. 2, *Pharm. Res.*, 5(6):369–371 (1988).

Database Medline, U.S. National Library of Medicine, Bethesda, MD. AN=8100696. Killackey et al., "Increased permeability of microcarrier–cultured endothelial monolayers in response to histamine and thrombin, a model for the in vitro study of increased vasoperemability," *Am. J. Pathol.*, 122(1):50–61 (1986).

Dehouck et al., *J. Neurochem.*, 54:1798 (1990).

Fitzer–Schiller, *The Washington Post*, p. D3 (Jan. 19, 1993).

Hardebo et al., *Acta Neuropathologica*, 51(1):33–38 (1980).

Hart, *J. Neuropath. Exp. Neurol.*, 46:141 (1987).

Hoffman et al., *Int. J. Cancer*, 42(3):382–388 (1988).

Ishikawa et al., *Anesthesiology*, 59(6):526–531 (Dec., 1983).

Joo et al., *Brain Res.*, 278(1–2):165–174 (1983).

Kumagai et al., *J. Biol. Chem.*, 262:15214 (1987).

Mohagheghpour et al., "The val–4/vcam–1 molecules participate in $\gamma\delta$ cell interaction with endothelial cells," *Cellular Immunology*, 143:170–182 (1992).

*Physician's Desk Reference*, Medical Exonomics Col, Diadell, N.J., pp. 1999–2004 (1993).

Rubin, "A cell culture model of the blood–brain barrier," *J. Cell Biol.*, 115:1725–1735 (1991).
Rutten *Brain Res.*, 425:301 (1987).
Tao–Cheng et al., *J. Neurochem.*, 7:3293 (1987).
Thorpe, *Trends in Biotech.*, 11:40–42 (1993).

Van Bree, *J. Pharm. Exp. Therap.*, 247:1233 (1988).
van Wezel, "Microcarrier cultures of animal cells; 7. cell propogation on culture supports," *Tissue Culture, Methods and Applications* (Kruse and Patterson, eds.), Academic Press, New York, 1973, pp. chapter 2:372–366.

COMPOSITIONS AND METHODS FOR MODULATING LEUKOCYTE ADHESION TO BRAIN ENDOTHELIAL CELLS

This application is a continuation of application Ser. No. 08/402,962 filed Mar. 10, 1995; which is a continuation of U.S. Ser. No. 07/871,223 field Apr. 17, 1992; (now abandoned) which is a continuation in part of U.S. Ser. No. 07/577,650 filed Sep. 4, 1990; (now U.S. Pat. No. 5,260,210) which is a continuation in part of U.S. Ser. No. 07/413,274 filed Sep. 27, 1989 (now abandoned); all of which are incorporated by reference.

BACKGROUND OF THE INVENTION

The present invention relates generally to compositions and methods for preventing or ameliorating brain tissue inflammation, and more specifically, relates to compositions and methods for modulating leukocyte adhesion to brain endothelial cell receptors.

Leukocytes are white blood cells that travel continuously in the general circulation. At the site of an injury or other inflammatory stimulus, endothelial cells that line blood vessels become activated to express molecules that are adhesive for leukocytes. The mechanics of leukocyte adhesion to endothelial cells involves, in part, the recognition and binding of cell surface receptors on leukocytes to the corresponding cell surface molecules on endothelia. Once bound, the leukocytes migrate across the blood vessel wall to enter the injured site and release chemical mediators to combat infection. For reviews of adhesion receptors of the immune system, see generally, Springer, *Nature* 346:425–434 (1990), and Osborn, *Cell* 62:3–6 (1990), both of which are incorporated herein by reference.

Inflammatory brain disorders, such as experimental autoimmune encephalomyelitis (EAE), multiple sclerosis (MS) and meningitis, are examples of central nervous system disorders in which the endothelium/leukocyte adhesion mechanism results in devastating destruction to otherwise healthy brain tissue. Large numbers of leukocytes migrate across the blood brain barrier (BBB) in subjects with these inflammatory diseases. The leukocytes release toxic mediators that cause extensive tissue damage resulting in impaired nerve conduction and paralysis. See generally, Hickey, *Psychneuroimmunology II* (Academic Press 1990).

In other organ systems, researchers have had some success preventing tissue damage by inhibiting en mass migration of leukocytes across blood vessels. It has been shown that in spite of the initial insult following myocardial ischemia to heart tissue, if leukocyte binding to the endothelium at the damaged site is inhibited, the leukocytes do not enter the tissue and further damage is greatly ameliorated. Vedder et al., *Surgery* 106:509 (1989). Simpson et al., *J. Clin. Invest.* 81:624–629 (1988) disclose that the administration of a monoclonal antibody that binds to a leukocyte cell adhesion-promoting glycoprotein (Mol; CD11b/CD18) resulted in reduced injury to heart tissue because fewer neutrophils (a type of leukocyte) entered the heart tissue. Hession et al. in International Patent Publication WO 90/13300, published Nov. 15, 1990, report that antibodies specific for various endothelial adhesion molecules (ELAMS) inhibit the binding of such ELAMS to cultured umbilical vein endothelial cells. Similarly, Wayner in WO 91/03252, published Mar. 21, 1991, describes the ability of monoclonal antibodies to block the adhesion of fibronectin to various hemapoietic cells, including those derived from human spleen, tonsil and peripheral blood.

Brain endothelium, however, is physiologically different from the endothelium associated with other organs, including those described in the above studies. Moreover, the expression of cell adhesion molecules is not predictable and may vary widely in response to different inflammatory stimuli and in different anatomical locations. For example, Tuomanen et al., *J. Ex. Med.* 170:959–968 (1989), show that antibodies directed against the CD18 family of adhesion-promoting receptors block the migration of leukocytes across the blood brain barrier (BBB) in response to acute inflammatory stimulus of bacterial origin. However, anti-CD18 was shown not to block leukocyte migration to the lung when stimulated by streptococcal infection, T. M. Carlos and J. M. Harb, *Immun. Rev.* 114:5–28 (1990). Furthermore, antibodies directed against the adhesion molecule VLA-4 are not sufficient by themselves to block monocyte (a type of leukocyte) entry into the inflamed peritoneum. As a consequence of the uniqueness of brain endothelium, compounded by the apparent multiplicity and specificity of the cell adhesion molecules in general, progress in identifying specific cell adhesion molecules and their complementary leukocyte receptors as well as the nature of their interaction has been slow.

One leukocyte cell surface receptor that has received attention from researchers is VLA-4, first identified by Hemler and Takada, EP 330,506, published Aug. 30, 1989. VLA-4 is a member of the $\beta1$ integrin family of cell surface receptors, each of which is comprised of two subunits, an $\alpha$ chain and a $\beta$ chain. VIA-4 contains an $\alpha4$ chain and a $\beta1$ chain. There are at least six $\beta1$ integrins, all sharing the same $\beta1$ chain and each having a distinct $\alpha$ chain. These six receptors all bind a different complement of the various cell matrix molecules, such as fibronectin, laminin, and collagen. VLA-4, for example, binds to fibronectin. VLA-4 is unique in that it also binds non-matrix molecules that are expressed by endothelial cells. At least one of these non-matrix molecules is called VCAM-1, which is expressed on cytokine-activated human umbilical vein endothelial cells in culture. Distinct epitopes of VLA-4 are responsible for the fibronectin and VCAM-1 binding activities and each activity has been shown to be inhibited independently. Elices et al., *Cell* 60:577–584 (1990).

One of the monoclonal antibodies used, HP2/1, reacts with the $\alpha$ chain of VLA-4 and blocks binding to both VCAM-1 and fibronectin. It does not affect the activity of the other members of the $\beta1$ integrin family. However, the $\alpha$ chain of VLA-4 also interacts with a distinct $\beta$ chain, called 62 7 (formerly called $\beta p$). This receptor mediates lymphocyte binding to intestinal lymphoid tissues. For example, HP2/1, reacting with $\alpha4$, blocks the activity of the intestinal receptor, i.e., $\alpha4\beta7$ (illustrated in Table 2). The monoclonal antibody, AIIB2, reacts with the $\beta1$ chain that is common to all members of the $\beta1$ integrins and potentially immunoreacts with the entire family, including the fibronectin and the VCAM-1 binding activities of VLA-4. It would not be expected to inhibit lymphocyte binding to intestinal endothelium, however, since this interaction appears to involve $\alpha4$ associated with $\beta7$ rather than $\beta1$. Prior to the present invention it was not known whether there existed an adhesion molecule on brain endothelial cells complementary to the VLA-4 receptor and, if one existed, whether VLA-4 binding to it could be modulated by these or other reagents.

Due to the unique nature of brain endothelial cells, the unpredictability of leukocyte/endothelial receptor interaction and, prior to the filing of U.S. Ser. No. 07/413,274, the unavailability of an effective in vitro BBB model on which tests could be conducted, little has been learned about the different types of adhesion molecules expressed on brain endothelial cells during brain inflammation, and little has been accomplished to ameliorate the effects of chronic inflammatory brain diseases, such as MS.

Accordingly, a need exists for compositions and methods for modulating the adhesion of leukocytes to brain endothelial cells. There also exists a need for methods of preventing or ameliorating brain inflammation characteristic of diseases such as MS. The present invention satisfies these needs and provides related advantages as well.

SUMMARY OF THE INVENTION

The present invention relates to methods of modulating the adhesion of leukocytes to brain endothelial cells. More specifically, reagents characterized by their ability to inhibit the binding of VLA-4 leukocyte cell surface receptors to brain endothelial cell adhesion molecules are administered in accordance with the methods of the present invention to inhibit the binding of leukocytes to brain endothelial cells. Compositions effective in modulating leukocyte adhesion to brain endothelial cells are also provided.

The present invention also relates to methods and compositions for preventing or ameliorating brain inflammation characteristic of diseases characterized by brain inflammation, such as MS. More specifically, by modulating the adhesion of leukocytes to brain endothelial cell receptors, the adverse effects of leukocyte migration across the BBB can be prevented.

Finally, the present invention provides methods of inducing brain inflammation by intracranial injection of tumor cells. These methods can be incorporated into assay formats useful for identifying brain anti-inflammatory compounds.

DETAILED DESCRIPTION OF THE INVENTION

Figure 1:
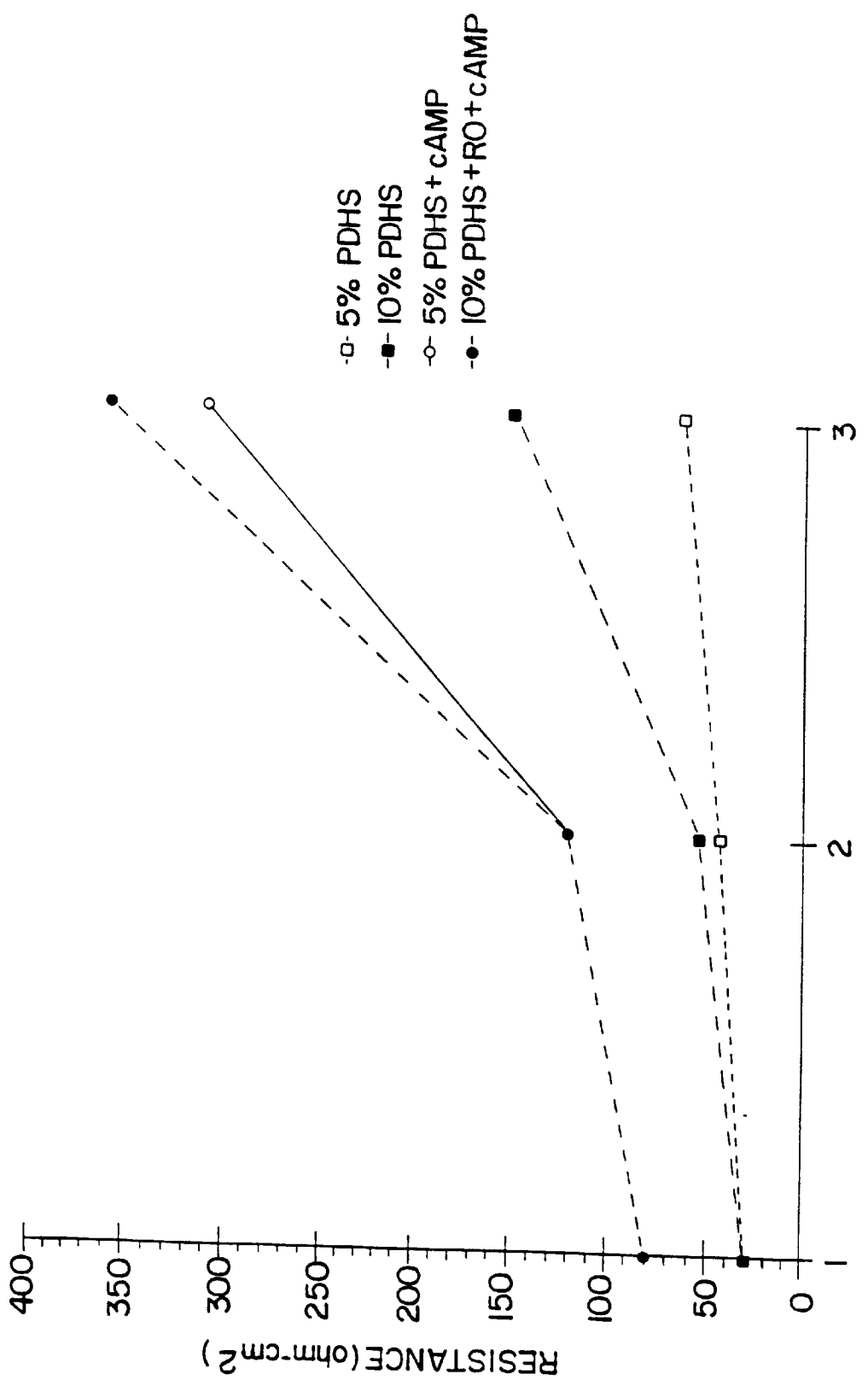
FIG. 1 provides transmonolayer electrical resistance data for the BBB model of the invention using bovine brain capillary endothelial cell cultures.

The present invention provides methods for modulating leukocyte adhesion to brain endothelial cells. Such methods are useful for ameliorating or preventing brain inflammation. Also provided are therapeutic compositions useful for treating brain inflammatory diseases such as MS.

In a non-diseased, healthy subject, leukocytes function as an integral part of a body's immune response to invading matter, such as bacteria or viruses. Adhesion proteins on the surface of endothelial cells at or near the site of injury or infection are expressed in response to such stimuli. Receptors on the surface of circulating leukocytes recognize and bind to the adhesion proteins expressed on the surface of these activated endothelial cells, enabling the migration of leukocytes across the blood vessel walls to the site of the injury or infection. The leukocytes then release chemical mediators to combat the invading matter.

Victims of diseases such as MS, EAE and meningitis suffer from indiscriminate destruction of brain tissue caused by the release of toxic mediators by leukocytes which errantly migrate across the BBB. For the first time, the present invention exploits the previously unknown interaction between the VLA-4 leukocyte cell surface receptor and its complementary brain endothelial cell adhesion molecule to modulate leukocyte adhesion to brain endothelial cells. Furthermore, for the first time, data is provided which demonstrates that certain blockers of VLA-4 are sufficient by themselves to substantially inhibit the binding of certain leukocytes to brain endothelium. Therefore, the present invention provides methods of preventing or ameliorating inflammation and destruction associated with diseases like MS.

To determine whether VLA-4 has a complementary adhesion protein on brain endothelial cells and to identify compositions and reagents useful for the methods of the present invention, two assay systems were employed. First, using a BBB model described in detail in Example 1.B, brain endothelial cell samples were activated with inflammation mediators. To a panel of these activated cell samples, leukocytes were introduced in the presence of different putative cell adhesion modulators for each sample. Individual samples were assayed for the presence or degree of leukocyte adhesion. Various reagents directed against VLA-4 (a leukocyte cell adhesion molecule) were shown to block lymphocyte binding to brain endothelium.

A separate assay produced the same results. Essentially, slices of brain tissue were analyzed for their ability to bind leukocytes in the presence of putative cell adhesion modulators. In this system, another novel aspect of the present invention was developed. Rats were injected intracranially with human tumor cells in order to induce inflammation in the brain. Previously, it was not known that this method could induce traffic across the BBB into the brain. Further, the type of inflammation induced is very much like that seen in MS victims where inflammation is characterized by small vessels with activated, almost cuboidal, endothelium. The vessels appear very similar to the "high endothelial venules" seen in lymphoid tissues. This appearance is consistent with the idea that the endothelial cells have become activated to support a great deal of cell traffic. Further, the vessels are surrounded by a cusp of lymphocytes, and active lymphocyte traffic is apparent. While MS-type inflammation has been observed in some rat systems, it has never before been induced by this method. Thus, the induction of brain inflammation using tumor cells has utility for obtaining tissue for an in vitro model of multiple sclerosis.

After an appropriate length of time, rat brains in which inflammation had been induced were removed and sectioned. To these sections, leukocytes were added in the presence of the putative cell adhesion modulator to be screened. Here too it was found that the anti-VLA-4 antibodies inhibited leukocyte adhesion to brain endothelium.

Figure 4:
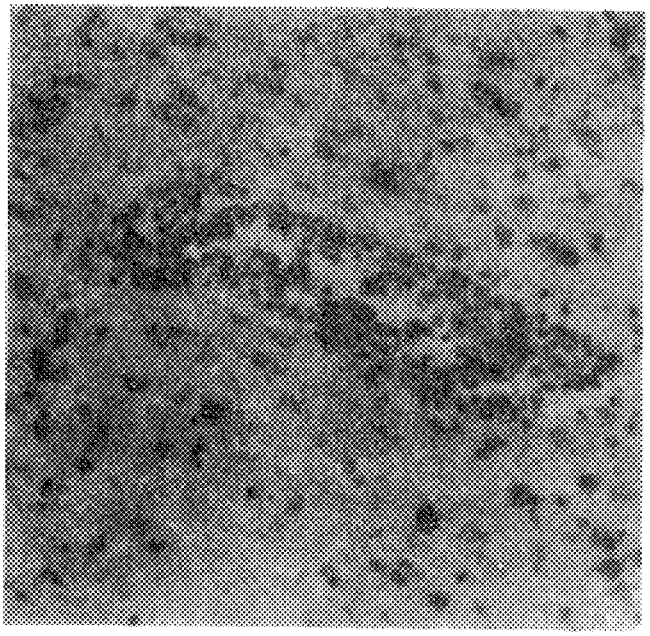
FIG. 4 (A–B) Panels A and B are photomicrographs of sections from a brain in which multiple sclerosis-type inflammation was induced via intracranial injection of human tumor cells. Human and mouse lymphocytes were allowed to contact the sections, and, as seen in Panel A, bind selectively to exposed brain endothelium. In Panel B, the lymphocytes were treated with an antibody that inhibits the human VLA-4 receptor (AIIB2, an anti-human $\beta$1 integrin) and as can be seen, the human lymphocyte (large cell) binding is substantially inhibited.
Figure 4:
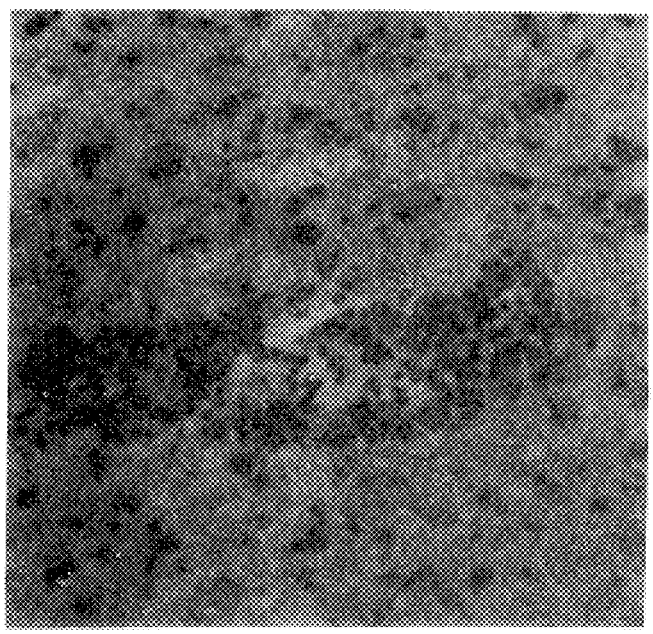
Figure 5:
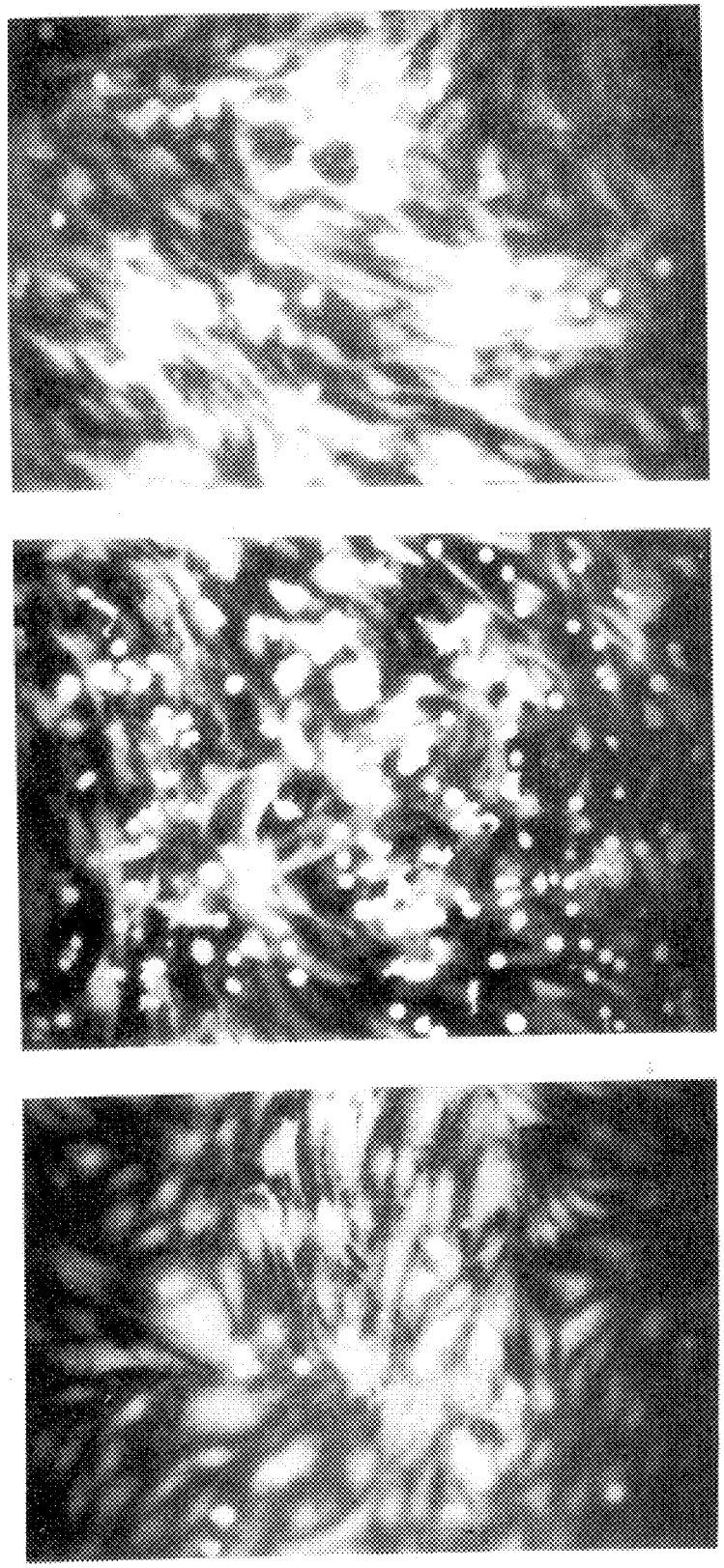
FIG. 5(A–C) is a photograph showing lymphocyte binding and inhibition of binding in brain endothelial cells in culture. Panel A shows the low level binding of lymphocytes to the BBB model endothelium. In Panel B, the endothelium has been treated with an inflammatory reagent and lymphocyte binding is increased substantially. In Panel C, the lymphocytes were pretreated with anti-human $\beta$1 integrin monoclonal antibody (AIIB2), and their binding to the stimulated endothelium was substantially inhibited.
Figure 6:
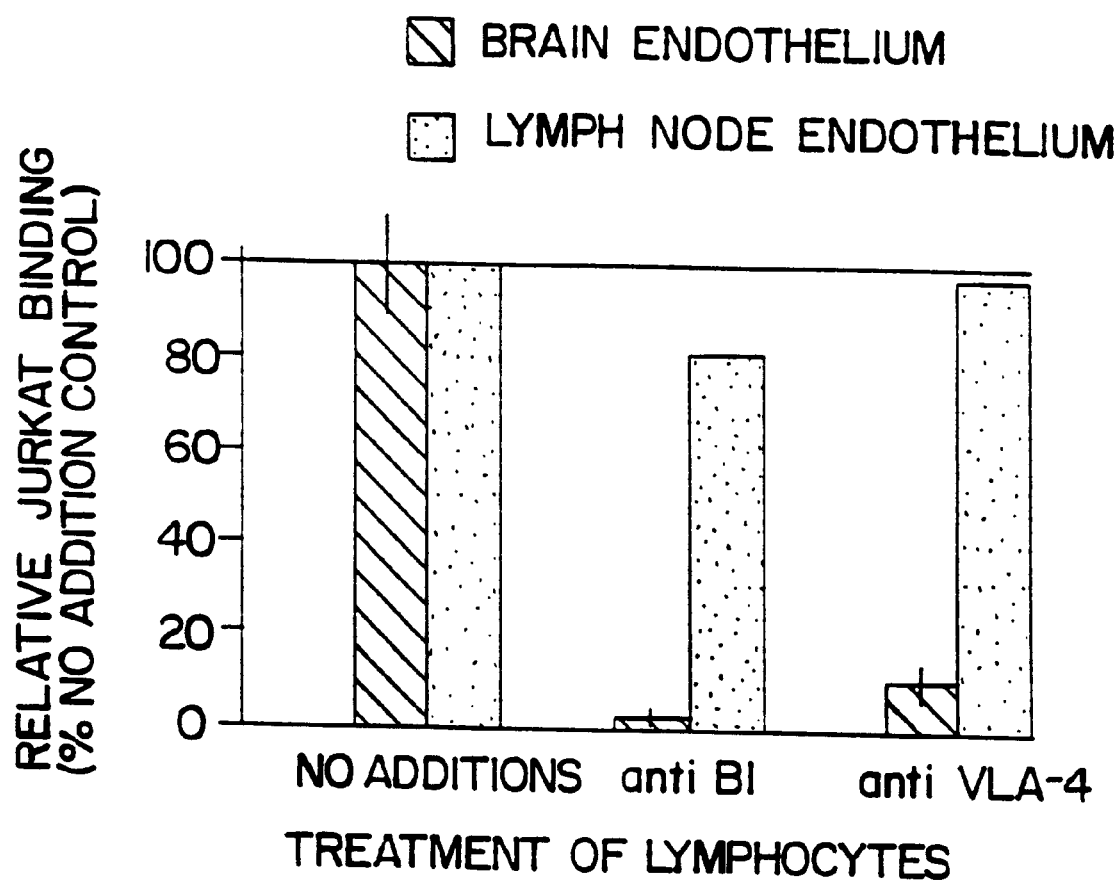
FIG. 6 is a graph showing the relative degree of lymphocyte binding to blood vessels in sections of inflamed brain tissue, and, as a basis for comparison, normal lymph node tissue. The "no additions" column shows brain tissue (scored) and lymph node endothelium (solid) to which untreated lymphocytes have been added. The degree of binding is represented as 100%. In the next two columns, lymphocytes have been pretreated with anti-VLA-4 reagents. The middle bars show lymphocytes pretreated with anti-$\beta$1 monoclonal antibody (AIIB2), the right-hand bars show lymphocytes pretreated with anti-$\alpha$4 monoclonal antibody (HP2/1). In both cases, lymphocyte binding in brain tissue was almost completely inhibited, as compared to the control. Lymphocyte binding to lymph node endothelium, in both cases, was not significantly inhibited.
Figure 7:
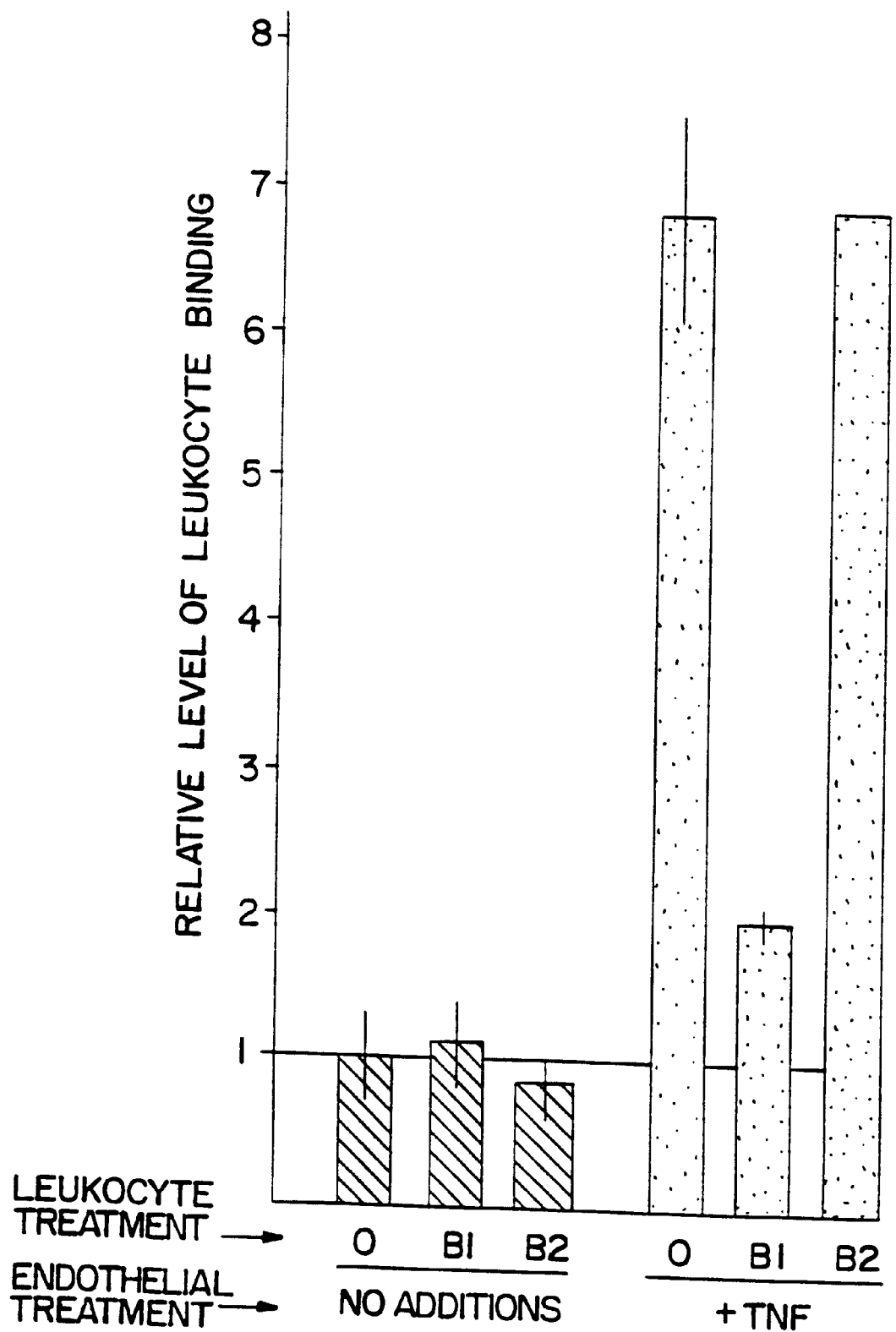
FIG. 7 is a graph showing the relative degree of Jurkat T-cell lymphocyte binding to brain endothelial cells in the blood brain barrier system. As can easily be seen, the anti-$\beta$1 antibody (AIIB2) effectively inhibited the binding of leukocytes to TNF-$\alpha$ activated brain endothelial cells. Anti-$\beta$2 (P4H9), as a control, on the other hand, approached the untreated control. Plainly, the $\beta$1 subunit provides an effective target for preventing VLA-4/VCAM-1 interaction in the brain.

This inhibition is graphically illustrated in the accompanying Figures. FIG. 4, Panel A shows a brain section in which no antibody was added. The small dark dots are leukocytes against the background of inflamed brain endothelial cells. As can be seen, the leukocytes are quite densely bound to the vessels in inflamed tissue. FIG. 4, Panel B shows inhibition of binding by antibodies directed against the β1 subunit of VLA-4. FIG. 5 shows a brain endothelial culture to which lymphocytes have bound. Panel A illustrates binding to unstimulated endothelium. Panel B shows binding to endothelium stimulated for twelve hours by TNFα. In Panel C, the lymphocytes have been pretreated with anti-β1 integrin (AIIB2) and their binding to TNFα-stimulated endothelium is greatly inhibited. As described in Example 1 below, the binding of human leukocytes to brain sections was confirmed by using an internal standard population of mouse leukocytes, a population not recognized by the anti-human reagent. This quantification confirmed the visual observation that anti-VLA antibodies prevented leukocyte binding to brain sections in which MS-type inflammation had been induced (FIG. 6). Further, leukocyte binding to cultured endothelium was quantified by prelabeling the cells with $^{125}I$; the inhibitory effects of anti-β1 are illustrated in FIG. 7.

Different cell adhesion molecules are expressed in different tissues in response to a variety of stimuli. Brain specificity can be beneficial in administering a leukocyte adhesion modulator for therapeutic purposes. Other tissues, apart from brain tissue, were analyzed in order to determine if either the anti-α4(HP2/1) or the anti-β1 (AIIB2) antibody had any immune reaction in those tissues. As shown in more detail in Example 1, the anti-α4 (HP2/1) inhibited lymphocyte binding to normal intestinal lymphoid tissue, but did not affect binding to normal lymph nodes. The anti-β1 (AIIB2) antibody does not inhibit binding to lymph nodes and would not be expected to affect binding to intestinal lymphoid tissue. However, unlike anti-α4, anti-β1 would be expected to disrupt numerous other adhesive interaction throughout the body since it would affect all six known β1 integrins. Thus, anti-α4 would be more specific than anti-β1. Most specific would be a reagent that recognizes α4 only in conjunction with β1. Such a reagent would not be expected to affect migration into the intestine.

Reagents which selectively react to block VLA-4 binding to brain endothelium may also be tested in experimental autoimmune encephalomyelitis (EAE). EAE is an inflammatory condition of the central nervous system with similarities to multiple sclerosis (Paterson in Textbook of Immunopathology, eds. Miescher and Mueller-Eberhard, 179–213, Grune and Stratton, N.Y. 1976).

EAE may be induced in rats by a single intraperitoneal injection of a CD4-positive T-cell clone specific for myelin basic protein. Inflammation is initiated within 4 to 12 hours; endogenous monocytes and lymphocytes infiltrate inflamed vessels in the brain stem and spinal cord, leading to paralysis of the tail and hind limbs by day 4 or 5.

Sections of EAE brain were tested for their ability to support leukocyte attachment using, for example, an in vitro binding assay described in Stamper and Woodruff, *J. Exp. Med.* 144:828–833 (1976). Reagents against leukocyte adhesion receptors were examined for inhibitory activity in the in vitro section assay described in Example 2. As shown in Table 4 and FIG. 8 herein, the attachment of U937 cells (a human monocytic cell line) was almost completely blocked by antibodies against human VLA-4 integrin. The anti-VLA-4 antibodies produced significantly greater blocking effect as compared to antibodies against other adhesion molecules.

Surprisingly, antibodies that selectively inhibit the fibronectin binding activity of a4 integrin (P4G9 and HP1/7) enhanced U937 attachment to the EAE vessels. These results suggest that fibronectin-binding activity of α4 integrin is not directly involved in U937 adhesion to EAE vessels in vitro. Table 4 also shows that antibodies against many other leukocyte adhesion receptors were without effect on U937 or lymphocyte binding to EAE vessels.

Given the in vitro results using the α4β1 reagents described above, the effect of these antibodies on the progression of EAE can also be tested in vivo by measuring the delay in the onset of paralysis or reduction in severity of the paralysis. The protective effect of one of the antibodies useful in the present invention, HP2/1, is provided in Example 2b. Thus, therapy based on inhibiting α4β1 integrin, or the ligand for this receptor, on brain endothelium can be useful in treating inflammatory diseases such as MS.

Additional reagents effective for inhibiting leukocyte binding to brain endothelial cells were identified by use of adhesion assays. Using HP2/1 as a control, antibodies were screened for their ability to inhibit the binding of lymphocytes to a known ligand for α4β1 integrin. Several additional reagents were identified that inhibit adhesion by targeting the α4 subunit of the VLA-4 leukocyte cell surface receptor. Monoclonal antibodies useful in the methods and compositions of the present invention include for example HP2/1, TY21.6, TY21.12 and L25. These antibodies react with the α chain of VLA-4 and block binding to VCAM-1, fibronectin and inflamed brain endothelial cells but do not affect the activity of the other members of the β1 integrin family.

Other reagents which selectively react against the VLA-4/VCAM-1 target are also envisioned. For example, an antibody which interacts with the VCAM-1 binding domain VLA-4 (α4) in conjunction with the β1 chain would block only lymphocyte migration into sites of inflammation, such as the brain during multiple sclerosis. This reagent further would not affect matrix interactions (mediated by all members of the β1 integrins) nor would it affect normal intestinal immunity (mediated by VLA-4αβ7). The production of this and other such reagents are well within the skill of the art.

The VLA-4/VCAM-1 molecules, instrumental in brain inflammation (particularly MS-type brain inflammation), provide molecular targets that can be put to a variety of uses. The present invention thus encompasses these uses and related compositions.

First, as is shown by Examples 1 and 2, reagents against the VLA-4 receptor can be used to modulate leukocyte adhesion to brain endothelial cells. Herein, the term "reagent" is used to denote a biologically active molecule that binds to a ligand receptor. For example, antibodies or fragments thereof which immunoreact with the VLA-4 receptor can be useful to prevent leukocyte binding to brain endothelial cells. Peptides, or peptidomimetics or related compounds, which can act to bind the cell surface receptor, are also contemplated, and can be made synthetically by methods known in the art. Other reagents that react with a VLA-4 receptor will be apparent to those skilled in the art.

Additionally, reagents against a VCAM-1-type adhesion molecule can be used to modulate leukocyte adhesion to brain endothelial cells. Either way, one cell adhesion molecule is blocked, and one pathway of leukocyte adhesion is inhibited.

It should be recognized that for therapeutic purposes, therapeutically effective compositions for preventing or ameliorating brain inflammation containing such VLA-4 or VCAM-1 directed reagents are contemplated as being within the scope of the present invention. For example, therapeutic compositions including at least one VLA-4 reagent or VCAM-1 reagent as well as other therapeutic compositions could be used to prevent or ameliorate brain inflammation. Another example is the use of a VCAM-1 reagent to which is attached a drug useful for treating MS or other inflammatory condition as a drug delivery vehicle which also prevents the adhesion of leukocytes to the VCAM-1 cell adhesion protein. Peptides, or peptidomimetics or other such molecules, which serve to substantially mimic one cell adhesion molecule or the other could be used in competition therapy wherein such peptides or peptidomimetics or other such molecules compete for the available locations on the surface of either the leukocyte (if substantially mimicking VCAM-1 or other VLA-4 ligand) or the endothelial cell (if substantially mimicking VLA-4).

Suitable pharmaceutical carriers and their formulations are described in Martin, REMINGTON'S PHARMACEUTICAL SCIENCES, 15th Ed. (Mack Publishing Co., Easton 1975). Such compositions will, in general, contain an effective amount of the active reagent together with a suitable amount of carrier so as to prepare the proper dosage form for proper administration to the subject. Useful pharmaceutical carriers for the preparation of the pharmaceutical compositions can be solids, liquids or gases; thus, the compositions can take the form of tablets, pills, capsules, powders, enterically coated or other protected formulations (such as by binding on ion exchange resins or other carriers, or packaging in lipid protein vesicles or adding additional terminal amino acids), sustained release formulations, solutions (e.g., ophthalmic drops), suspensions, elixirs, aerosols, and the like. Water, saline, aqueous dextrose, and glycols are preferred liquid carriers, particularly (when isotonic) for injectable solutions. The carrier can be selected from various oils including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like.

In the practice of the therapeutic methods of the present invention, an effective amount of the active compound, including derivatives or salts thereof, or a pharmaceutical composition containing the same, as described above, is administered via any of the usual and acceptable methods known in the art, either singly or in combination with another compound or compounds of the present invention or other pharmaceutical agents such as anti-inflammatory agents, or other therapeutics known to have an effect on inflammation or the like. These compounds or compositions can thus be administered orally, sublingually, topically (e.g., on the skin or in the eyes), parenterally (e.g., intramuscularly, intravenously, subcutaneously or intradermally), or by inhalation, and in the form of either solid, liquid or gaseous dosage including tablets, suspensions, and aerosols, as is discussed in more detail above. The administration can be conducted in single unit dosage form with continuous therapy or in single dose therapy ad libitum.

In one embodiment, the therapeutic methods of the present invention are practiced when the relief of symptoms is specifically required or perhaps imminently so. In another embodiment, the method is effectively practiced as continuous or prophylactic treatment.

In the practice of the therapeutic methods of the invention, the particular dosage of pharmaceutical composition to be administered to the subject will depend on a variety of considerations including the nature of the disease, the severity thereof, the schedule of administration, the age and physical characteristics of the subject, and so forth. Proper dosages may be established using clinical approaches familiar to the medicinal arts. It is presently believed that dosages in the range of 0.1 to 100 mg of compound per kilogram of subject body weight will be useful, and a range of 1 to 100 mg per kg generally preferred where administration is by injection or ingestion. Topical dosages may utilize formulations containing active compound and a liquid carrier or excipient, with multiple daily applications being appropriate.

Imaging reagents are also contemplated. A tracer molecule, detectable in radiographic or other imaging techniques could be linked to an anti-VCAM-1 or anti-VLA-4 reagent to identify areas of active leukocyte traffic in the brain. These imaging reagents are useful in diagnostic protocols and in determining the progression of the disease or the effectiveness of therapy, for example.

Also provided by the present invention is a method of inducing brian inflammation by intracranial injection of tumor cells. One type of tumor cell useful for inducing brain inflammation by this method is ATCC 1573, a human kidney-derived cell line.

The invention further provides an assay for ascertaining whether a compound is effective as an anti-inflammatory agent in the brain which exploits the method described above. More specifically, the assay includes inducing brain inflammation in a living organism by intracranially injection tumor cells and subsequently exposing the brain tissue to the putative brain anti-inflammatory agent.

Other uses, formulations, compositions, and processes will be readily apparent to those skilled in the art. The following examples are illustrative of several embodiments of this invention, and should not be construed as in any way limiting the invention as recited in the claims.

EXAMPLE 1

Modulation of Leukocyte Adhesion to Inflamed Brain Endothelial Cells

In this embodiment, antibodies against VIA-4 were shown to substantially prevent leukocyte adhesion to brain endothelium using both a novel system for inducing multiple sclerosis-type inflammation in vivo and a blood brain barrier model.

Unless otherwise stated, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. As set forth above, all publications to which reference is made are incorporated herein by reference.

Materials and Methods

Lymphocytes: Mouse or rat lymphocytes were isolated immediately before a binding assay from mesenteric, cervical and brachial lymph nodes by standard methods and crushed between the frosted ends of two glass slides. Human lymphocytes were isolated from heparinized or EDTA-treated whole blood using Mono/Poly separation medium (Flow Labs, Mclean, Va.), and used immediately.

Lymphoid Cell Lines: All cell lines were obtained from the cell culture facility at the University of California, San Francisco and were maintained in RPMI-1640 with 10% FBS (37° C., 10% CO2). RPMI-1460 was purchased from the University of California, San Francisco. These University of California cell lines are all made available to the public. Specifically, the cell lines obtained from the University of California, San Francisco are the Jurkat T-cell line, U937, THP-1, FRO, HL60, and HUT78. These cell lines may also be available from other sources.

Monoclonal Antibodies: AIIB2, against human $\beta 1$ integrin (the "anti-$\beta 1$"), is available from Dr. Caroline Damsky, Department of Oral Biology, University of California, San Francisco. HP2/1, against VLA-4 (the "anti-$\alpha 4$") was purchased from AMAC, Inc. (Westbrook ME, Product #0764). The HP2/1 also cross-reacts with rat lymphocytes. P4H9, against human $\beta 2$ integrin (the "anti-$\beta 2$") was purchased from Telios, Inc. (San Diego, Calif., Product #A052). This anti-$\beta 2$, against the $\beta 2$ integrin is not known to react with any subunit of VLA-4.

When used to treat lymphocytes, the anti-$\beta 1$ (AIIB2) hybricoma supernatant was used at a 1:2 dilution. The anti-$\alpha 4$ (HP2/1) antibody was purified by the manufacturer, and used at a 5 $\mu$g/ml concentration. The anti-$\beta 2$ (P4H9) was purified by the manufacturer, and used at 5 $\mu$g/ml. For treatment of lymphocytes, the lymphocytes were mixed with the above concentrations of antibody, and allowed to incubate on ice for about 30 minutes prior to use. The cells were washed to remove unbound antibody, and resuspended in RPMI to a typical concentration of $10^7$ cells/ml.

Other tissue sections: In the frozen brain section assay, the preparation of brain sections is described below. Lymph node and intestinal tissues were removed from rats, and sectioned as described for brain tissues, below.

A. In vitro Frozen Brain Section Assay

In order to establish inflammatory brain lesions that involve a large degree of immune cell infiltration, rats were injected in the brain with human kidney cell line 293 (American Type Culture Collection, ATCC No. 1573). This method was found to stimulate the entry of all leukocyte classes into the brain in a predictable time course. The trauma of the injection induces the entry of neutrophils and monocytes within minutes, which continues for about 24 to about 48 hours. The presence of the human cells serves as a persistent irritant to the immune system, stimulating further leukocyte infiltration, including that of lymphocytes. Typically, by about day 6, lymphocytes and monocytes are the major infiltrating leukocyte classes, entering in such large numbers so as to produce cellular cuffs around small blood vessels in the brain near the injection site. The speed and predictability of this procedure has made it ideal for obtaining brain tissue that can be used in the in vitro assay described below. In this assay, the brains are quickly frozen and sectioned. Leukocytes (immortalized and grown as cell lines, or freshly isolated from rodents or humans as described above) are then exposed to the sections, and, if they express the appropriate receptors, adhere selectively to the exposed profiles of activated endothelium near the inflammatory lesion. The leukocytes do not bind to nonactivated endothelium in the brain sections away from the inflammatory lesion or within sections of the non-stimulated control brain.

Rats (male Sprague-Oawley, 275–300 g), were anesthetized with Nembutal (60 mg/kg-i.p.) and mounted in a stereotaxic device. The head was shaved and an incision was made to reveal the dorsal skull. Holes were drilled through the skull on the left and right side overlying the parietal cortex. $10^7$ human kidney derived cells (ATCC 1573 cell line), suspended in PBS, were delivered to the parietal cortices in a volume of 10 $\mu$l. It is believed that other allogeneic cells or cell lines would also induce the present MS-type symptoms via these methods. For example, we have used primary bovine microvascular endothelial cells to induce a similar inflammatory reaction.

The incision was sutured and the animal allowed to recover for 1–10 days. On the appropriate day, brains were removed from animals that had been anesthetized with halothane and killed by cardiac puncture. The cerebellum was removed and the brains were then placed rostral side down on a mound of gum tragacanth (mixed with water to the consistency of thick paste) and frozen by immersion for 60 seconds in 2-methyl butane chilled on dry ice. The brains were then stored in sealed tubes at −80° C.

Immediately before the assay, 10 micron thick brain sections were cut on a cryostat and transferred to the center of a 14 mm well, pre-formed within a thin epoxy coating (Catalog #100314, Carlson Scientific, Inc., Peotone, Ill.) and allowed to air-dry at room temperature. The transfer was accomplished by touching the slide (at room temperature) to the section, which was still on the cold knife blade. Sections of control tissues (peripheral lymph nodes and Peyer's patches, isolated from noninjected rats, frozen and stored as described above) were usually placed adjacent to the brain sections in the same wells. The slides were positioned on a metal tray resting on ice and the wells were filled with 100 μl of the appropriate cell suspension. The metal tray and supporting ice were then gyrated at about 50 to about 80 rpm for 30 minutes on an orbital shaker (Lab Line Instruments, Inc., Model 3520, with 1 inch diameter rotation). The cell suspension was then decanted and the slides were carefully placed vertically in PBS with 2.5% glutaraldehyde on ice for 20 minutes. The slides were then dipped 5 times in PBS, placed in 0.5% toluidine blue (20% EtOH) for 1 minute, destained with 2 brief dips in 100% ethanol, covered with Immu-mount™ mounting medium (Shandon, Sweickley, Pa.), and cover slipped.

Herein, cell suspensions used were freshly isolated rat, mouse or human lymphocytes, the U937 human myelomonocytic cell line, and the Jurket human T cell line. Cell lines THP-1, FRO, HL60 and HUT78 were found not to bind with stimulated brain sections, and were not further analyzed in the brain section assay.

The degree of lymphocyte binding was quantified by one of two methods. The first relied upon an internal reference population of cells, similar to that described by Butcher, et al., *J. Immunol.* 123:1996–2003 (1979). The second method was based on the absolute number of lymphocytes bound to blood vessels in a given tissue section. For the internal reference method, populations of lymphoid cell lines were mixed with freshly isolated lymphocytes of a different species (e.g., human cell lines with mouse lymphocytes) so that both were at a final concentration of $3-5 \times 10^7$/ml. Aliquots of the mixed population were then treated with species-specific antibodies for 30 minutes on ice. In general, the cells were washed out of the antibody prior to the binding assay. Binding was quantified by determining the ratio of two different populations of leukocytes bound to blood vessels. It was always arranged such that the leukocyte populations could readily be distinguished by size— lymphoid cell lines are large cells, generally greater than 20 μm in diameter, while lymphocytes are small cells, less than 10 μm in diameter. Thus in an experiment with human T cell line mixed with rat lymphocytes, the degree of inhibition produced by an anti-human monoclonal antibody (compared to control antibodies or to no treatment) was quantified by determining the ratio of large to small cells bound. The results obtained are presented in Table 1, below. As can be seen, use of an anti-VLA-4 reagent significantly inhibited binding of immune cells to brain cells displaying MS-type inflammation. These results are also shown in FIG. 4, which clearly displays the inhibitory effect of the anti-VLA-4 reagents.

TABLE 1

| Treatment Used | Ratio large/small | % Control Jurkat Binding |
| --- | --- | --- |
| No treatment | 2.08 ± 0.17 | 100 ± 8 |
| anti-β1 (AIIB2) | 0.02 ± 0.01 | 1 ± 0.5 |
| anti-α4 (HP2/1) | 0.23 ± 0.15 | 11 ± 7 |

The second method of quantification compared a single population of leukocytes treated in different ways in adjacent assay wells. The degree of inhibition was determined by comparing the number of leukocytes bound to all vessels in a given tissue section under treated and untreated conditions. Tissue sections were prepared as described above. The degree of binding was quantified as the actual number of rat lymphocytes bound to the blood vessels within the sections. These data are presented in Table 2, below.

In addition, lymph node tissue was also tested, and these data are displayed in FIG. 6. All reagents were prepared as described above. Here, anti-β1 (AIIB2) antibody and anti-α4 (HP2/1) antibody were both shown to inhibit Jurkat T-cell lymphocyte binding to brain sections, but not to lymph node sections.

These data confirm that anti-VLA-4 reagents showed substantial inhibition of leukocyte binding to brain tissue displaying the features of MS-type inflammation.

TABLE 2

Quantification of rat lymphocyte binding to different tissue sections by comparing the number of lymphocytes bound to all vessels under treated and untreated conditions. Four replicates were used for each treatment, and raw data are presented in parenthesis below the mean.

| Treatment | Brain | Intestinal | Lymph Node |
| --- | --- | --- | --- |
| No treatment | 24(100%) | 43(100%) | 21(100%) |
|  | (24/24/32/18) | (35/45/42/50) | (25/27/18/15) |
| anti-VLA-4α | 2(8%) | 6(15%) | 20(95%) |
|  | (2/3/2/2) | (3/3/5/10) | (14/30/22/12) |

B. Preparation of the Blood Brain Barrier Assay

Origin of Astrocytes: Purified populations of neonatal rodent brain type 1 astrocytes were prepared according to the procedures of Lillien et al. (Lillien, L. E., *Neuron,* 1:485 (1988)). In brief, cerebral cortices were removed from neonatal rats, white matter was discarded, and the gray mater mechanically and enzymatically (trypsinization) dissociated. Cells were plated in polylysine-coated flasks in Dulbecco's Modified Eagle's Medium (DMEM) plus 10% fetal calf serum (FCS). After 5 days, loosely attached cells were dislodged by shaking, attached cells were passaged into new flasks, and treated with cytosine arabinoside (an anti-mitotic drug) to remove actively proliferating contaminating cells. Finally, astrocytes were maintained in a chemically defined medium and fed twice weekly. Cell type was determined by reactivity with particular sets of antibodies. For example, type 1 astrocytes are fluorescently labeled by an antibody against glial fibrillary acidic protein, but not with the monoclonal antibody A2B5 (which labels type 2 astrocytes) or with an anti-galactocerebroside antibody (which labels oligodendrocytes) (Raff, M. C., et al., *J. Neurosci.,* 3:1289 (1983)).

Origin of Capillary Endothelial Cells: Endothelial cells are prepared from a variety of animal and human sources. For example, mixed populations of endothelial cells may be prepared from purified capillaries derived from rodent and bovine brain, bovine retina, bovine adrenal, bovine aorta, and human omentum or from human umbilical vein. Bovine sources are particularly suitable because of the large amounts of tissue available, the ready availability of fresh tissues, and the similarity of the permeability of bovine capillary cells to that of their human counterparts.

Bovine brain microvascular cells were isolated according to Audus et al., *Pharm. Res.,* 3:51 (1986)). Briefly, a slurry of brain grey matter in Liebovitz' L-15 medium was homogenized, and the microvascular cell-containing particular fraction was separated on a Dextran cushion. Capillaries were resuspended and homogenized, then passed through a series of nylon filters. Capillaries were digested further with collagenase plus trypsin to provide a population of single mixed endothelial cells. These cells were plated on a collagen or fibronectin treated substratum in 10% plasma-derived horse serum (PDHS) in Dulbecco's modified Eagle's Medium (DMEM). Rat brain microvascular endothelial cells were prepared similarly according to Bowman, et al. (Bowman, P. D., et al., 17:353 (1981)). Briefly, brain grey matter is minced and digested with collagenase and dispase. The particulate matter is separated over a 25% bovine serum albumin (BSA) cushion, and the pellet further digested with collagenase and DNase. Finally, endothelial cells are isolated on a Percoll gradient, and washed cells are plated on a collagen-treated substratum in DMEM 20% plasma-derived horse serum (PDHS) 150 µg/ml endothelial cell growth supplement (ECGS, available from Sigma Chemical Co., St. Luis, Mo.) (McGuire, P.C., et al., *Lab. Invest.*, 57:94 (1987)).

Alternatively, rat brain microvascular endothelial cells (RBEC) were isolated using another method. The brains were cleared of meninges, and the grey matter minced, homogenized and filtered through a 155 µm Nytex filter. Capillary fragments were then digested with collagenase and trypsin. Isolated cells were plated in collagen-coated flasks and grown in RBEC medium (50% astrocyte-conditioned medium, 50% DMEM with 10% calf serum complemented with bovine retina factor, non-essential amino acids, sodium pyruvate, penicillin-streptomycin, glutamine and β-mercaptaethanol).

Bovine brain microvascular endothelial cells can also be isolated according to the above method and grown in BBEC-medium (50% astrocyte conditioned medium, 50% MEM with 10% PDHS).

Cells are identified as endothelial by immunofluorescence assay with anti-von Willebrand protein (rabbit serum from Bering Diagnostics, La Jolla, Calif.) and uptake of di-I-labeled acetylated LDL (Molecular Probes, Junction City, Oreg.). Endothelial cells are typically passaged once a week and maintained in BBEC-medium.

Endothelial cell cultures can be cloned, if desired, using the cloning ring technique. Cells are plated in at low density (1000 cells per 10 cm plate) in 10% FCS. Plastic cloning rings, dipped in silicone grease, are placed on cells so as to encircle and isolate single or paired cells on an inverted microscope. Once the clone expands, or preferably, immediately after the ring is in place, the cells are detached by trypsinization within the ring and transferred to a well of a multi-well culture disk. Multiple clones of microvascular endothelial cells from bovine brain, bovine aorta, rat aorta, and rat brain can be isolated by this technique.

Astrocyte-Derived Conditioned Medium: Neonatal rat brain type 1 astrocytes were grown to confluency in poly-D-lysine-coated 75 $cm^2$ flasks. Fresh medium was added to the cells, and removed after 2–4 days. The medium was filtered through a 0.2 µm Millipore filter, and stored frozen at −80° C. in small aliquots.

Figure 3:
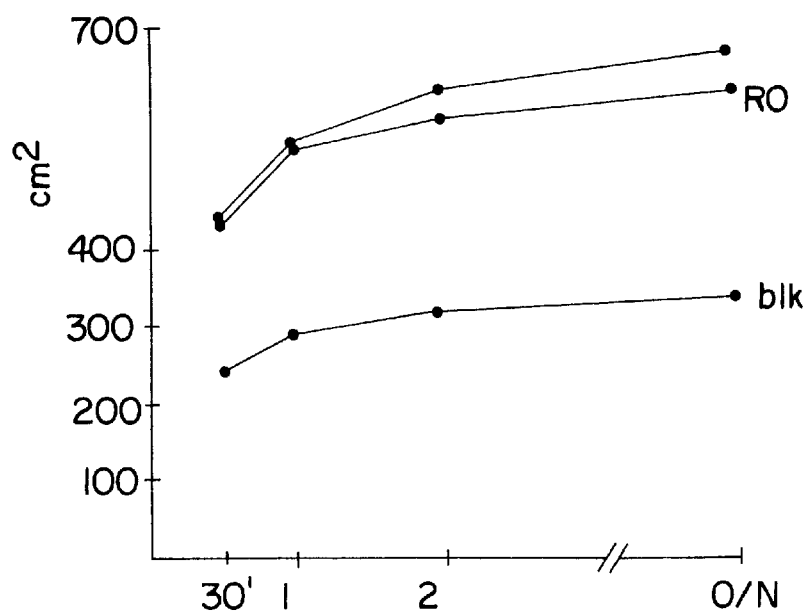
FIG. 3 shows the effects of different classes of cyclic AMP phosphodiesterase inhibitors on tight junctions of bovine brain endothelial cells in the BBB in vitro model. Cells were isolated, grown on permeable filters, and maintained in astrocyte-derived conditioned medium but were not treated with agents that elevate cyclic AMP levels in such cells. At the beginning of the experiment (i.e., in a low resistance state), cells were either left untreated (blk in FIG. 3) or treated with 17.5 $\mu$M Rolipram or RO-20-1724 (specific inhibitors of cyclic AMP phosphodiesterase) (RO in FIG. 3). In both experiments, resistance was already substantially higher in cells treated with these compounds by 30 minutes.
Figure 3:
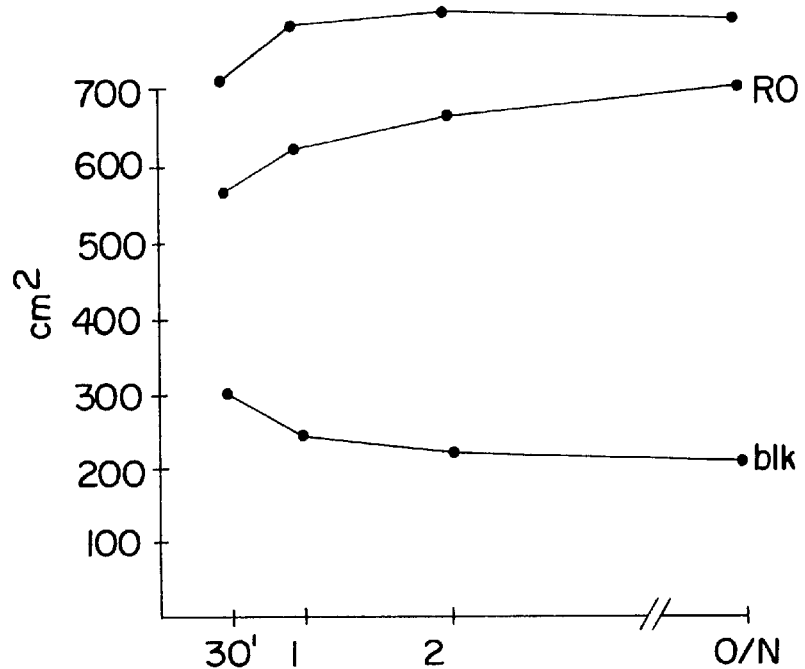

Elevation of Cyclic AMP Concentrations: Cultures of endothelial cells were treated with one or more agents known to increase cyclic AMP concentrations. These include, but are not limited to: 1) from about 10 to about 100 µM of a β-adrenergic agent, such as isoproterenol, that binds to specific β-adrenergic receptors on cell surfaces and stimulates G-protein-mediated activation of adenylate cyclase; 2) serotonergic compounds such as 5-hydroxytryptamine; 3) forskolin (Sigma Chem. Co., St. Louis, Mo.), an agent that directly activates adenylate cyclase; 4) parathyroid hormone; and 5) calcitonin gene related peptide. Adding an inhibitor of cyclic AMP phosphodiesterase, the enzyme that degrades cyclic AMP to adenylic acid, will accentuate the cyclic AMP elevating effects of the aforementioned modalities; examples of such inhibitors are 4-(3-butoxy-4-methoxybenzyl)-2-imidazolidinone (Hoffman-LaRoche. Nutley N.J.), theophylline and methylisobutylxanthine (Sigma Chem. Co.), Rolipram (Berlex, Inc.) and RO-20-1724 (BioMol, Inc., Plymouth Meeting, Pa.). For example, see FIG. 3 herein. In addition, certain derivatives of cyclic AMP can be used to elevate the effective cyclic AMP concentration in such cells; such derivatives include 8-bromo cyclic AMP (Sigma Chem. Co) and 8-(4-chlorophenylthio)cyclic AMP (Boehringer-Mannheim Corp., Indianapolis, Ind.). By "effective cyclic AMP" we mean endogenous cyclic AMP or cyclic AMP derivatives to which endothelial cells are permeable and which act physiologically as does endogenous cyclic AMP within such cells. By "effective cyclic GMP" we mean endogenous cyclic GMP or cyclic GMP derivatives to which endothelial cells are permeable and which act as does endogenous cyclic GMP within such cells. By "physiological action" of cyclic AMP or cyclic GMP or derivatives thereof we mean those immediate biochemical reactions of these cyclic nucleotides that lead ultimately to the physiological actions ascribed to them. For example, cyclic AMP activates certain protein kinases that catalyze the phosphorylation of hydroxyamino acid residues such as serine, threonine and tyrosine in particular proteins, such phosphorylation activating these proteins. Effects of cyclic AMP are reversed by phosphoprotein phosphatases that catalyze the de-phosphorylation of the aforementioned hydroxyamino acid residue-containing proteins.

It has also been discovered that the formation of tight junctions between endothelial cells in the BBB model used in the invention is substantially enhanced when endothelial cells are grown from the time of their isolation in the presence of astrocyte-derived conditioned medium (ADCM). Thus, when endothelial cells are passaged onto filters, e.g., Costar filters, they are preferably grown in a medium containing 50s ADCM made in MEM with 10% fetal calf serum and 50% N2 (a chemically-defined medium). After 2–3 days of growth on the filters, they may be treated with a cyclic AMP analogue and a cyclic AMP phosphodiesterase inhibitor (e.g., Rolipram or RO 20-1724).

In addition, it has been discovered that an elevation of actual or effective cyclic AMP concentrations, with consequent formation of tight junctions between mixed endothelial cells as determined by electrical resistance measurements, was also associated with substantial peripheral staining by phalloidin, a toxin produced by *Amanita phalloides* that is known to bind to filamentous actin and prevent their depolymerization (stryer, L., "Biochemistry", 3d., W. H. Freeman, N.Y. 1988, p. 940). The belt-like pattern of phalloidin staining in these treated endothelial cells is similar to that seen in epithelial cells exhibiting high resistance tight junctions. (Gumbiner, B., *J. Cell Biol.*, 107:1575 (1985).) In addition, when endothelial cells were grown with astrocyte-derived conditioned medium plus cyclic AMP enhancing agents such that peripheral phalloidin staining of cells was substantially present, transmonolayer electrical resistance was increased over that obtained in the absence of conditioned medium.

Construction of a Chamber BBB Model: In a general embodiment used in the invention, brain capillary endothelial cells are grown on a porous substratum-coated solid support, e.g., filters or membranes. It has been found that endothelial cells can attach to and grow on Nucleopore polycarbonate filters (Costar, Inc., Cambridge, Mass.), Millicell GM and HA porous nitrocellulose filters (Millipore Corp, Bedford, Mass.), and collagen membranes (ICN Biomedical, Inc., Costa Mesa, Calif.). The Millicell GM and Nucleopore polycarbonate filters required pre-treatment, i.e., coating, with extracellular matrix material (ECM, see below), components in order to promote adhesion of cells to the filter. Nucleopore filters promote media exchange across the filter, and permit cellular processes to cross through. Filters allow cells more completely to establish blood side and brain side domains, as they permit separate manipulation of the two compartments of the chamber.

Porous solid supports can be coated with ECM by soaking them in an aqueous solution of laminin, vitronectin, or fibronectin (typically, from about 10 to about 50 $\mu$g/ml), Matrigel® (an extract of FHS sarcoma obtainable from Collaborative Res., Bedford, Mass.) in PBS, type I rat tail collagen or type IV collagen in dilute acetic acid (Collaborative Research, Inc., Collagen Corp, and New York Blood Bank, N.Y.), or astrocyte extracellular matrix (AECM).

In one embodiment, microvascular endothelial cells were disposed on an extracellular matrix (ECM)-coated porous solid support as described above, but astrocytes were absent from either the contralateral side of the porous solid support or from a surface of the chamber. Instead, the growth medium in the blood compartment of the chamber, i.e., the compartment opposite that which houses endothelial cells, was supplemented with from 0% to 100% with astrocyte-derived or endothelial cell-derived conditioned media, or with brain or other tissue extracts, obtained as described above, as required.

Agents that are intended to elevate intracellular concentrations of cyclic AMP in endothelial cells or to increase the concentration of effective cyclic AMP may be added to the growth medium, as can be dyes, e.g., trypan blue or Evans blue, or other macromolecules that are used to test for tight junction resistance.

Assay for Tight Junctions: The presence of tight junctions in the endothelial layer of the BBB model can be detected using reagents that recognize proteins associated with tight junctions. For example, the monoclonal antibody 40.76, made against Z0-1 tight junction protein, specifically recognizes an antigen on both bovine and mouse endothelial cells (Anderson, J. M. et al., *J. Cell Biol.*, 106:1141 (1988); Stevenson, R. B., et al., *J. Cell Biol.*, 103:755 (1986)). This approach allows the user to detect the formation of tight junctions among small subsets of endothelial cells, and to refine culture conditions to enhance the formation of tight junctions.

The degree of tightness of tight junctions can be also assessed by transcellular electrical resistance measurements. For transendothelial cell resistance measurements, cells were grown on a porous solid support, e.g., a filter or membrane attached to a holding device in order adequately to suspend the cellular monolayer, such as the Costar Transwell apparatus or the ICN Cellogen. Transmonolayer resistance is measured, for example, with the device of Perkins et al. (Perkins, F. M., et al., *Am. J. Physiol.*, 241:C154 (1981)). Cells were maintained in a growth medium or physiological saline, and calomel electrodes on each side of the endothelial cells are connected by a saturated KCl—3% agar bridge. Current is passed between two Ag-Agcl electrodes and the voltage measured with a Keithly multimeter. Resistance is calculated from the change in voltage across the monolayer induced when a short current pulse (10–100 mamp) is applied. The resistance of the filter or membrane alone is subtracted. The resistance, multiplied by the surface area of the filter or membrane, yields the resistance in ohms-cm2.

Bovine brain capillary endothelial cells were grown on polycarbonate filters in a conditioned growth medium containing either 5% or 10% PDHS. In controls, the growth medium contained 5% PDHS (□) or 10% PDHS (■). In experimental cultures, the growth medium was supplemented with either 5% PDHS+250 $\mu$M 8-(4-chlorophenylthio) cyclic AMP (○) or 10% PDHS+250 $\mu$M 8-(4-chlorophenylthio) cyclic AMP+35 $\mu$M RO-20-1724, a cyclic AMP phosphodiesterase inhibitor (●). Transmonolayer electrical resistances were then determined; these are shown in FIG. 1.

The cyclic AMP analogue alone greatly increased transmonolayer electrical resistance, which is indicative of tight junction formation. Resistances of about 400 ohm-cm$^2$ were obtained with monolayers treated with both the cyclic AMP analogue and an agent (RO-20-1724) that inhibited degradation of cyclic AMP.

As noted above, peripheral binding of the toxin phalloidin reveals the presence of belt-like filamentous actin, a hallmark of tight junction formation among endothelial cells. Staining of filamentous actin by phalloidin can be visualized using derivatives such as phalloidin coumarin phenylisothiocyanate or fluorescent FITC-phalloidin or TRITC-phalloidin (Signma Chem. Co., St. Louis, Mo.).

Another means for assessing the formation of tight junctions among endothelial cells is to determine the transport of macromolecules from the apical blood side to the abluminal brain side. For example, the water-soluble dye Evans blue (mol. wt. 960) that binds strongly to albumin (Freedman, F. B., et al, *Am. J. Physiol.*, 216:675 (1969)), can be used to assess the tightness of newly formed endothelial cell junctions; tissues with tight junctions that exclude the dye or exhibit limited transport will remain white, whereas those without tight junctions or that exhibit significant transport capabilities will be stained blue as the dye passes through the junctions. Other water-soluble, macromolecular markers for tight junction formation include fluorescein isothiocyanate bound to dextran (FITC-dextran. mol. wt. 20,000, Sigma Chem. Co.) and $^{125}$I-labeled albumin (DuPont/KEN, Wilmington, Del.). Fluorescent dextrans of other sizes and sodium fluorescein itself may be used as well.

Still another means for assessing the tightness of junctions among endothelial cells in the blood-brain model of the invention is to compare the transport of a hydrophilic compound, e.g., sucrose, and a hydrophobic compound of similar size, e.g., chlorambucil, across filters with and without monolayered endothelial cells. When the transmonoloayer resistance is high, the transport of sucrose should be low compared to that of chlorambucil (or other hydrophobic compounds of similar size). Alternatively, when the resistance is high, the transport of sucrose should be much less (e.g., 50-fold or more) than across cell-free filters. Contrariwise, in "leaky" cell junctions, the relative transport of sucrose will be substantially increased.

Figure 2:
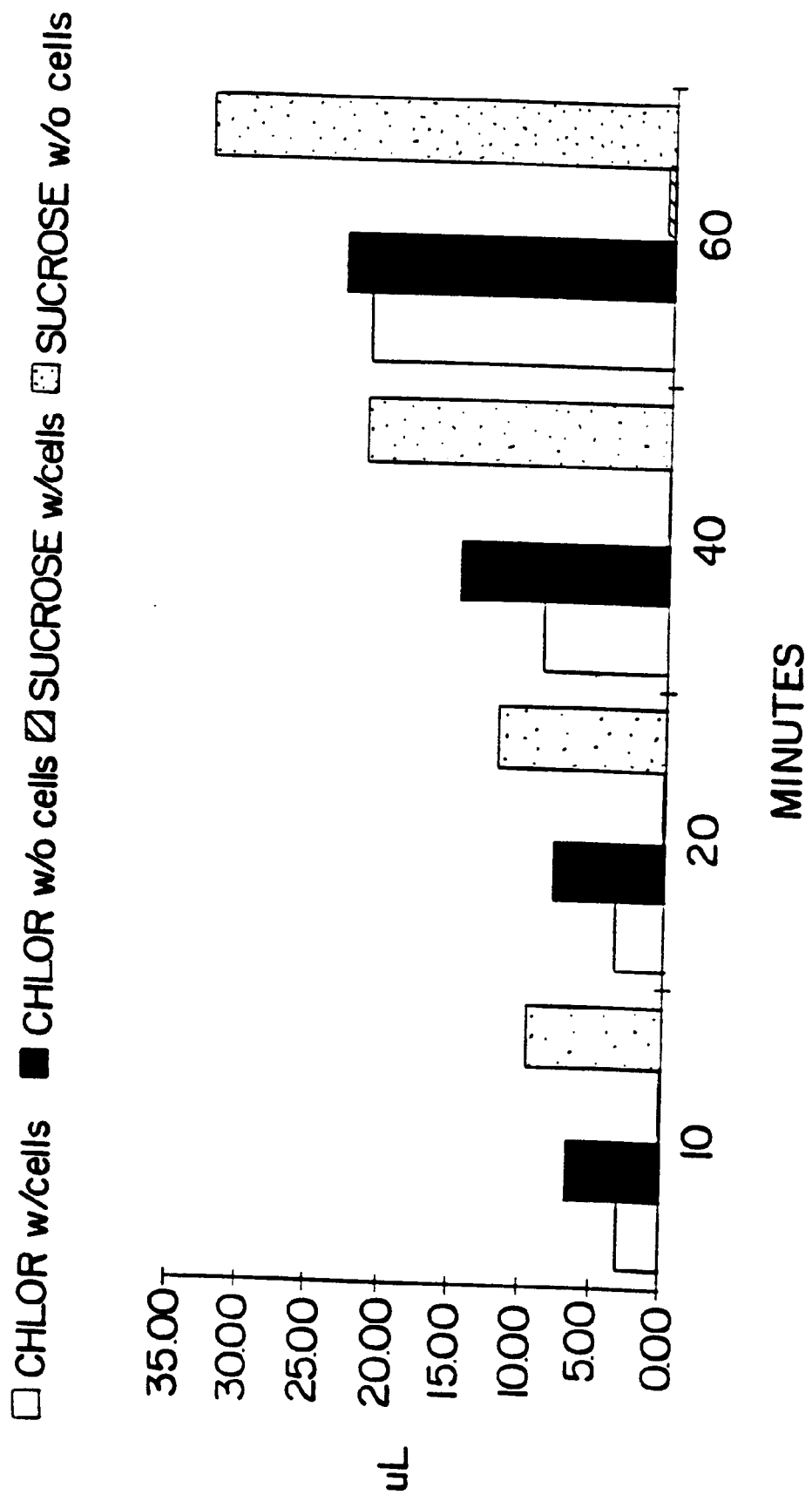
FIG. 2 shows flux data for sucrose and chlorambucil across tight junctions of brain endothelial cells.

FIG. 2 shows transport data across high resistance monolayers of bovine endothelial cells on filters in the blood-brain model, using labeled sucrose (360 dalton, hydrophilic) and labeled chlorambucil (304 dalton, mildly hydrophobic antitumor compound).

Although these compounds are of similar size, the hydrophobic compound was transported much better than was the hydrophilic compound across filters with cells, compared to transport rate across cell-free filters.

Sucrose was almost entirely prevented from leaking between the cells. This is a significant advance over previous models in which the difference in the rate of sucrose across filters with and without cells was 3 to 5-fold due to leaky tight junctions in those models.

Assessment of Ligand Binding, Transcytosis and Drug Delivery: The access in the model of the invention to both sides of a differentiated endothelium or EGM-coated porous solid supports permits the assay of specific binding and uptake of radiolabeled ligands from an apical (luminal) or basolateral (abluminal) aspect. Furthermore, by adding a labeled probe to one side of the porous solid support, one can assess the ability of the probe to be transcytosed from one side of the monolayer to the other.

The model also allows for testing the access of potential new therapeutics to the brain parenchyma. For example, drugs such as L-DOPA can cross the BBB, being recognized and transported by amino acid transporters. Lipophilic drugs are also able to penetrate the BBB. However, as indicated above, potentially therapeutic drugs that are not lipophilic and for which no specific transport mechanism exists may be unable to penetrate the BBB or may do so at rates insufficient to maintain a therapeutic drug level in the brain. The in vitro model of the BBB of this invention can also be used to test tight junction-disrupting compositions. It has been found by immunohistological methods that a molecule immunologically related to the mouse cell-adhesion molecule E-cadherin is present on mouse endothelial cells. The expression of the E-cadherin-like molecule is enhanced in cultures of brain endothelial cells exhibiting increased resistance (see Example 9 of WO91/05038).

C. Leukocyte Binding to Cultures of Blood Brain Barrier Endothelial Cells

Bovine or human brain endothelial cells were maintained in accordance with the blood-brain barrier model as described above. In experiments where the endothelium was activated, 5 $\mu$l of stimulating agent was added directly to the lower chamber medium (800 $\mu$l) of the culture system. Here, TNF$\alpha$ (Amgen Biologicals, Thousand Oaks, Calif.) was added to the lower chamber for a final concentration of 400 units/ml. In activation, PMA-S (in DMSO) was found not to be effective in stimulating lymphocyte binding, but other activating agents are known, and will be apparent to those skilled in the art.

In this manner, the endothelial cells were exposed to the agent on their ablumenal surface, as would be the typical situation during an inflammatory reaction in the brain. Immediately before the assay, the electrical resistance of the cultures was measured and the filters (supporting the endothelial cells) were washed at room temperature by dipping in three separate vats of D-MEM with 1% FBS and 20 mM Hepes (200 mls each). The filters were then placed in fresh wells containing the same medium and the assay was performed at room temperature.

Typically, 10 $\mu$l of leukocytes (at a preferred concentration of $10^7$/ml) in the presence or absence of test reagents, were added to the upper chamber of the culture system, such that the leukocytes would encounter the lumenal or blood side of the endothelium, as they would in the brain vasculature. Here, leukocytes were rat, mouse or human lymphocytes, the U937 human myelomonocytic cell line, and the Jurket human T cell line as described above. The lymphocytes were pretreated with anti-$\beta$1 (AIIB2) or anti-$\beta$2 (P4H9) antibody as described above.

Cell lines THP-1 and FRO were also found to bind to brain endothelial cells stimulated with TNF$\alpha$, but HL60 and HUT78 did not so bind. U937 binding was found not to be inhibited by exposure to anti-$\beta$1 (AIIB2).

The culture plates were placed on a gyratory shaker at about 100 rpm for 30 seconds, then allowed to sit undisturbed at room temperature for about 30 minutes. The assay was terminated by gently washing the filters in PBS with 1% glutaraldehyde (dipping and pouring three times at different angles). The glutaraldehyde causes the cells to fluoresce under the proper optical conditions, as described below. The filters were then allowed to fix in the glutaraldehyde solution undisturbed for 60 minutes.

The degree of leukocyte binding to the filters was examined in one of two ways. In the first, the bound cells were visualized directly. The filter was cut free of the culture well apparatus and mounting on glass slides with Immumount™. The filters were examined with an immunofluorescence microscope set for rhodamine or fluorescein optics, and observing the cells by glutaraldehyde-induced autofluorescence.

The results of the immunofluorescence assay can be visualized in FIG. 5. As is easily visualized, the density of Jurkat T-cell lymphocytes pretreated with anti-$\beta$1 (AIIB2) antibody is far lower (Panel A) than the binding density for untreated leukocytes (Panel B). This graphically depicts the anatomical and physiological reaction when a reagent is used to block the VCAM-1l/VLA-4 interaction between brain endothelial cells and leukocytes.

In the second method, the leukocytes were prelabeled with a radioactive tracer and the degree of binding was quantified by measuring the amount of radioactivity associated with the entire endothelial surface on the culture filter. Prelabeling of lymphoid cell lines was accomplished by the addition of 1 uCi/ml 125IUDR (Amersham #IM.355V) obtained from the Amersham Corporation, Arlington Heights, Ill.) to the standard culture medium approximately 12–20 hrs. before the assay. The cells were washed free of unincorporated label by three separate washes in 15 mls of fresh bench medium (RPMI-1640 with 5% FBS and 25 mM Hepes). Concentration was then adjusted to $10^7$ cells/ml in the presence or absence of test reagents. Again, all of the above lymphocytes were used (rat, mouse or human lymphocytes, the U937 human myelomonocytic cell line, and the Jurket human T cell line) as described above. The lymphocytes were pretreated with either anti-$\beta$1 (AIIB2) or anti-$\beta$2 (P4H9) antibody as described above. Also, the lymphocytes were pretreated with HP2/1 as described above.

The assay was carried out as above, except that at the end the isolated filters are placed in tubes and counted in a gamma counter (Beckman Corporation, Model 5500B) for 1 minute. The results are presented in Table 3 below. As can be seen, the samples that contained anti-VLA-4 reagents show far lower radioactivity levels the controls. These data confirm the results from the above fluorescence data, namely, that the binding of anti-VLA-4 to the VCAM-1 adhesion molecule is substantially inhibited by reagents which would prevent binding at that locus.

These data are also presented in FIG. 7 which shows the relative degree of Jurkat T-cell lymphocyte binding to brain endothelial cells in the blood-brain barrier system. As can easily be seen, the anti-$\beta$1 (AIIB2) antibody effectively inhibited the binding of leukocytes to TNF$\alpha$ activated brain endothelial cells. Anti-$\beta$2 antibody (P4H9), as a control, on the other hand, approaches the untreated control. Plainly, the $\beta$1 subunit provides an effective target for preventing VLA-4 interaction with inflamed brain endothelial cells.

TABLE 3

This table shows the quantification of lymphocyte
binding via radioactive labelling of lymphocytes.

| Lymphocyte Type | Treatment | Count per Minute |
|---|---|---|
| Jurkat T-cell | | |
| | 0 (no TNFα) | 112; 273 |
| | AIIB2 (no TNFα) | 259; 156 |
| | P4H9 (no TNFα) | 198; 124 |
| | 0 (+ TNFα) | 1430; 1150 |
| | AIIB2 (+ TNFα) | 361; 385 |
| | P4H9 (+ TNFα) | 1313; (n/a) |

EXAMPLE 2

EAE Model of Brain Inflammation

Figure 8A:
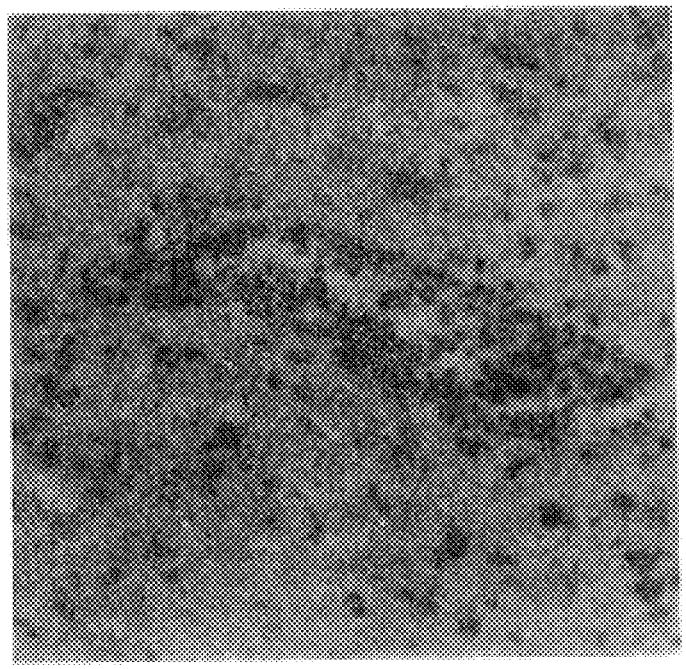
FIG. 8(A–B) shows the inhibition by anti-VLA-4 of human U937 cell binding to inflamed EAE vessels.
Figure 8B:
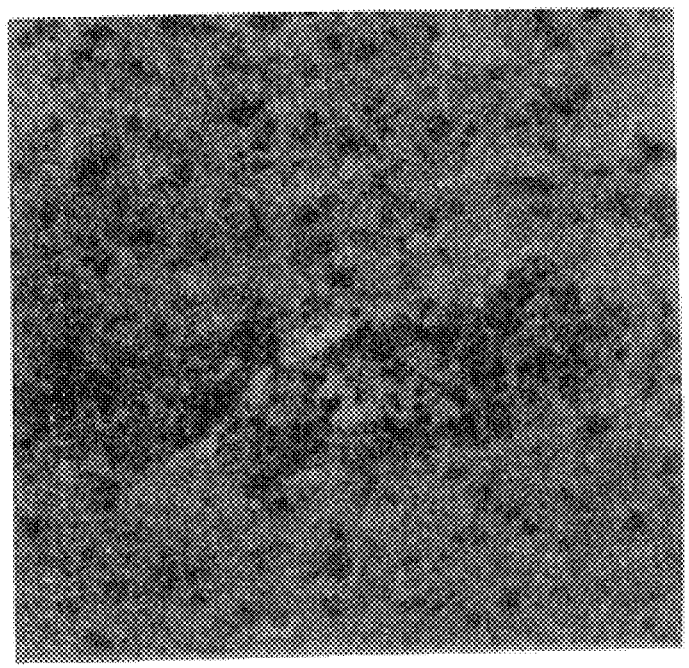

A. In vitro Analysis of Lymphocyte Binding to Inflamed Endothelium in Sections of EAE Brain Following the procedure described in Yednock et al. Nature 356:63–66 (1992), brains were removed from rats with EAE on day 5 of disease (first day of tail/hind limb paralysis). The brains were quickly frozen, sectioned, and overlayed with lymphoid cell suspensions (methods as described above for tumor injected brains). Human U937 cells bound selectively to inflamed vessels in the rat EAE brains (FIG. 8a). Pretreatment of the U937 cells with the anti-VLA-4 antibody, HP2/1, completely inhibited their binding to inflamed vessels in an adjacent section of EAE brain (FIG. 8b).

As shown in part a of Table 4, binding of human U937 cells to inflamed vessels in EAE brain was inhibited by reagents against VLA-4 (anti-α4, HP2/1; and anti-β2, AIIB2), but not by antibodies against numerous other adhesion receptors. Two antibodies that selectively inhibit the fibronectin (FN)-binding activity of VLA-4, did not affect U937 binding to the EAE vessels (P4G9 and HP1/7). Part b of Table 4 shows that binding of freshly isolated human lymphocytes and monocytes, as well as freshly isolated rat and mouse lymphocytes to the inflamed EAE vessels was also selectively inhibited by antibodies against VLA-4. The assay was performed as described above and the degree of binding was quantified using a reference population of cells (see above).

TABLE 4

| (a) Treatment of U937 Cells | Vessels Clone | Relative Binding to EAE (% of control) |
|---|---|---|
| Anti-β1 integrin | AIIB2 | 8 ± 3 |
| Anti-α3 integrin | A043 | 111 ± 5 |
| Anti-α4 integrin | HP2/1 (inhibits FN and VCAM-1-binding) | 3 ± 1 |
| Anti-α4 integrin | P4G9 (selectivity inhibits FN binding) | 151 ± 7 |
| Anti-α4 integrin | HP1/7 (selectively inhibits FN binding) | 338 ± 41 |
| Anti-α5 integrin | F1D6 | 104 ± 6 |
| Anti-α6 integrin | GoH3 | 88 ± 11 |
| Anti-α4 and -α5 | F4G9 and P106 (combined) | 138 ± 8 |
| Anti-α3, -α4, and -α6 | A043, P1D5, and GoH3 (combined) | 112 ± 3 |
| Anti-CD44 | Homos-3 | 107 ± 4 |
| Anti-L-selection | TQ-1 | 96 ± 4 |
| Anti-β2 integrin | P4H9 | 77 ± 1 |
| Anti-β2 integrin | TS1/18 | 98 ± 5 |
| Anti-β2 integrin | P4H9 (tested at 25° C.) | 100 ± 10 |
| Anti-β2 integrin | TS1/18 (tested at 25° C.) | 114 ± 2 |
| Anti-α4 integrin | HP2/1 (tested at 25° C.) | 5 ± 1 |
| Anti-LFA-1 | IOT1G | 123 ± 2 |
| Anti-Mac-1 | LM2/1 | 107 ± 3 |

| (b) Treatment of freshly isolated leukocytes or monocytes | | | |
|---|---|---|---|
| Antibody specificity | Clone | Cell Type | Relative Binding to EAE vessels (% of control) |
| Anti-β1 integrin | AIIB2 | human lymphocytes | 7 ± 2 |
| Anti-α4 integrin | HP2/1 | human lymphocytes | 0 ± 0 |
| Anti-α4 integrin | HP2/1 | human lymphocytes | 1 ± 1 |
| Anti-α4 integrin | HP2/1 | rat lymphocytes | 18 ± 7 |
| Anti-α4 integrin | R1-2 | mouse lymphocytes | 43 ± 2 |
| Anti-CD2 | OX-34 | rat lymphocytes | 100 ± 10 |
| Anti-L-selectin | MEL-14 | mouse lymphocytes | 92 ± 4 |
| Peyer's patch homing receptor | 18.2.6 | rat lymphocytes | 117 ± 12 |
| Anti-LFA-1 | OX-52 | rat lymphocytes | 87 ± 1 |
| Anti-CD45 | OX-1 | rat lymphocytes | 90 ± 3 |
| Anti-Thy 1.1 | OX-7 | rat lymphocytes | 87 ± 3 |
| Anti-CD4 | OX-35 | rat lymphocytes | 107 ± 8 |
| Anti-monocyte/T cell surface | OX-44 | rat lymphocytes | 102 ± 8 |

B. Effect of In Vivo Administration of Anti-VLA-4

Anti-VLA-4 was administered to rats (intraperitoneal administration) in order to determine the effect of the antibody on the progression of EAE.

For Table 5 below, in each experiment, the T-cell clone was administered on day 0. On day 2, animals received an intraperitoneal injection of PBS, the indicated amount of purified anti-α4 integrin, or the indicated amount of purified control antibody. All antibodies were mouse IgG$_1$. Disease was defined by complete tail or tail and hind limb paralysis. In animals that developed disease, paralysis began on day 4 or 5, peaked on day 5 or 6, and steadily diminished thereafter. Two additional experiments gave comparable results. Circulating levels and differential counts of white blood cells were indistinguishable between HP2/1-treated and PBS control animals when measured on days 3, 4 and 7 (day 3 is one day after antibody administration and one day before the earliest onset of paralysis). Bulk quantities of HP2/1 were purchased from AMAC; MOPC from Sigma; OX-1 and OX-7 from Bioproducts for Science.

Figure 9A:
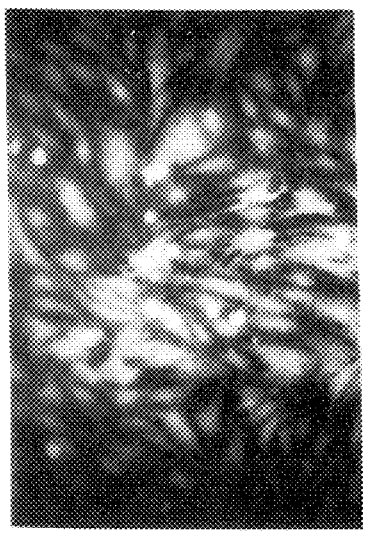
FIG. 9(A–B) shows in vivo administration of anti-VLA-4 prevents leukocyte infiltration into the brain during EAE.
Figure 9B:
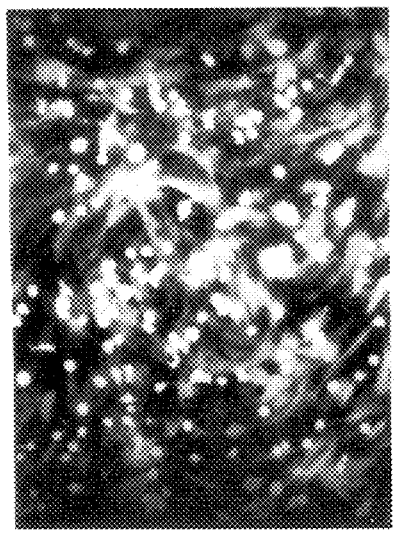
Figure 9C:

Brains were removed from several diseased EAE and healthy anti-α4 integrin-treated EAE rats from experiments 2 and 3 on day 6 (×70 magnification). The FIG. 9 micrographs show sections of comparable regions of the brainstem and cerebellum, immunostained with anti-CD45 (OX-1) to illustrate the degree of leukocyte infiltration. There was extensive infiltration in brains from diseased EAE animals as shown in FIG. 9a, whereas leukocytes could not be detected in the EAE rats treated with anti-α4 integrin (FIG. 9b).

TABLE 5

Experiment 1

| Treatment | Number of animals with paralysis | | |
|---|---|---|---|
| | Day 5 | Day 6 | Day 7 |
| No antibody | 4/6 | 5/6 | 4/6 |
| HP2/1 (1.2 mg) | 0/6 | 0/6 | 0/6 |
| MOPC (1.2 mg) | 6/6 | 6/6 | 5/6 |

Experiment 2

| Treatment | Number of animals with paralysis | | |
|---|---|---|---|
| | Day 4 | Day 5 | Day 6 |
| No antibody | 5/5 | 5/5 | 5/5 |
| HP2/1 (1.0 mg) | 0/4 | 2/4 | 2/4 |
| OX-1 (1.0 mg) | 5/5 | 5/5 | 5/5 |
| OX-7 (1.0 mg) | 5/5 | 5/5 | 5/5 |

Experiment 3

| Treatment | Number of animals with paralysis | | |
|---|---|---|---|
| | Day 4 | Day 5 | Day 6 |
| No antibody | 6/6 | 6/6 | 6/6 |
| HP2/1 (0.4 mg) | 1/5 | 2/5 | 2/5 |
| HP2/1 (0.8 mg) | 1/5 | 2/5 | 1/5 |
| HP2/1 (1.6 mg) | 0/6 | 0/6 | 2/6 |

EXAMPLE 3

Production of Additional VLA-4 Antibodies

A. Immunization and Screening Protocol

TY21.6 and 21.12 were raised against the human B cell line, Ramos (obtained from the ATCC). $10^7$ Ramos cells, homogenized in Freund's complete adjuvant, were injected into a Balb/c mouse (intraperitoneal administration). 14 days later the animal was boosted with another $10^7$ Ramos cells (homogenized in Freund's incomplete adjuvant, administered i.p.). After an additional 14 days, the animal was injected with $2 \times 10^6$ living Ramos cells (intravenous administration). Three days after the final boost, the spleen was removed, the splenocytes were isolated, fused with the SP/2 myeloma, and plated on approximately 2000 wells. Supernatants were screened for their ability to inhibit the human B cell line Ramos binding to VCAM-1 transfected L-cells. VCAM-1 transfected L cells were produced using standard techniques: VCAM-1 CDNA was isolated by PCR; primers were synthesized based on the published sequence and template RNA was isolated from TNF-stimulated human umbilical vein endothelial cells (HUVEC). The isolated cDNA was transfected into mouse L cells and clones expressing high levels of VCAM-1 message were isolated. For adhesion assays, VCAM-1 L cells were plated on 96 well plates and allowed to reach confluency. U937 cells were fluorescently labelled with PKH26 (Zynaxis Cell Science, Inc., Malvern, Pa.), pretreated with hybridoma supernatants for 30 minutes on ice (200,000 cells/sample), and added to individual VCAM-1 wells. Adhesion was allowed to occur for 30 minutes at room temperature, the wells were then washed to remove unbound cells, and the remaining cells were lysed with 40 ul of 0.1% Triton. 20 ul of the extract was analyzed on a Pandex plate reader to determine the degree of fluorescence (i.e., the number of cells bound). The degree of binding was determined by the percent of fluorescence relative to the fluorescence associated with the total number of input cells/well (i.e., 200,000 U937 cells). Two individual hybridomas were identified as potent blockers of Ramos binding to VCAM-1 and were stabilized as clones. They have been designated as TY21.6 and TY21.12.

It was determined that both antibodies react with α4 integrin since the antibodies precipitated two protein bands from a lysate of cell surface-labeled human lymphocytes. These proteins were 150 and 130 kD in molecular weight, which corresponds to the known molecular weights of the α4 and β1 integrin chains, respectively. Identical bands were precipitated in a parallel sample by a commercially available, well characterized antibody against human α4 integrin (HP2/1). No other protein bands were detected. These results suggest that 21.6 and 21.12 react with the α4β1 integrin complex.

TY21.6 and 21.12 were further characterized by FACS analysis, using standard methods for staining cells by indirect immunofluorescence. Both antibodies react with the human B cell line, JY (which expresses α4 integrin, but only low levels of β1). Both antibodies fail to react with human K562 cells or with human neutrophils (which express β1 but very low levels of α4 integrin). Finally, both antibodies react with mouse L cells transfected with human α4β1 integrin (produced as described above for VCAM-1 transfected L cells, using the human T cell line Jurkat for template RNA), but not with control transfected L cells. An identical pattern of reactivity was obtained with HP2/1, whereas a well characterized antibody against β1 integrin (AIIB2) did not react with JY, but did react with K562 and neutrophils. Thus, TY21.6 and TY21.12 selectively react with α4 integrin.

B. Functional Characterization of TY21.6, TY21.12 and L25

All three antibodies, TY21.6, TY21.12 and L-25 (Clayberger et al., *J. Immunol.* 138:1510–1514 (1987), effectively inhibit human lymphocyte binding to TNF-stimulated rat brain EC. Primary rat brain EC, or rat brain EC clones (described above) were plated on 96 well tissue culture plates. EC in some of the wells were stimulated with TNF (as described above) for 4–24 hours. Jurkat, U937, or Ramos cells were fluorescently labelled (as described above), pretreated with the indicated antibody, and then added to individual wells (200,000 cells/well; triplicate wells/antibody treatment). The degree of binding was determined as described above for the VCAM-1 96-well binding assay. The results are summarized in Table 6.

TABLE 6

| Exp. 1 | | Exp. 2 | | | |
|---|---|---|---|---|---|
| | % input | | | % Input Binding | |
| 1° Rat | cells | Clone | | | |
| Brain EC | U937 | bound | RBEC | Antibody | Jurkat | Ramos |
| 0 | no Ab | 7 ± 1 | 0 | no Ab | 3 ± 1 | 2 ± 1 |
| TNFα | no Ab | 36 ± 5 | TNFα | no Ab | 66 ± 3 | 40 ± 1 |
| TNFα | HP2/1 | 13 ± 2 | TNFα | HP2/1 | 6 ± 1 | 2 ± 1 |
| TNFα | 21.6 | 7 ± 1 | TNFα | TY21.6 | 8 ± 2 | 1 ± 1 |
| TNFα | 21.12 | 5 ± 2 | TNFα | TY21.12 | 8 ± 1 | 1 ± 0 |
| | | | TNFα | L25 | 12 ± 3 | 2 ± 1 |

All three antibodies were also found to inhibit human lymphocyte binding to VCAM-1 transfected L cells (assay as described above) as shown in Table 7.

TABLE 7

| Antibody | % Input Binding | |
|---|---|---|
| | Ramos | U937 |
| none | 45 ± 13 | 60 ± 6 |
| HP2/1 | 0 ± 0 | 3 ± 2 |
| L25 | 9 ± 2 | 11 ± 2 |
| TY21.6 | 1 ± 1 | 0 ± 1 |
| TY21.12 | 0 ± 0 | 1 ± 0 |

As shown in Table 8, all three antibodies inhibit cell binding to inflamed vessels in sections of EAE brain (assay peerformed as described above).

TABLE 8

| U937 Treatment | Binding |
|---|---|
| no antibody | 100 ± 10 |
| TY21.6 | 0 ± 1 |
| TY21.12 | 0 ± 1 |
| L25 | 1 ± 1 |
| HP2/1 | 3 ± 1 |

Some antibodies against α4 integrin (such as HP2/4, Pulido et al., *J. Biol. Chem.* 266:10241–10245 (1991)) induce lymphocytes to self aggregate. The basis of this aggregation is poorly understood. In the same report, L25 was reported to induce lymphocyte aggregation; however, we have not been able to reproduce those observations. In our hands, L25, TY21.6 and 21.12 do not induce cell aggregation when directly compared with HP2/4. Aggregation was induced by mixing 100,000 U937 cells with antibody supernatant (final dilution 1:5) in wells of a 96 well tissue culture plate (100 ul final volume/well). Aggregation was allowed to occur for 30 mrinutes to 4 hours, and scored visually with an arbitrary +/− rating system, compared to the no-antibody control. The results are shown in Table 9.

TABLE 9

| Inducing Antibody | Degree of U937 Aggregation |
|---|---|
| none | − |
| HP2/1 | − |
| L25 | − |
| TY21.6 | − |
| TY21.12 | − |
| HP2/4 | +++ |

Some antibodies against α4 integrin inhibit aggregation induced by the anti-α4 integrin antibody HP2/4. HP2/1, TY21.6 and TY21.12 block HP2/4 induced cell aggregation, whereas L25 does not. This assay was performed as above, except that the U937 cells were pretreated with the blocking antibodies (supernatant diluted 1:5 or purified antibody at 5 ug/ml) for 30 minutes on ice before addition of the aggregation-inducing antibody, HP2/4 (final concentration of HP2/4 ⁻hybridoma supernatant was 1:20).

TABLE 10

| Pretreatment of U937 | Degree of Aggregation Induced by HP2/4 |
|---|---|
| none | +++ |
| HP2/1 | − |
| L25 | +++ |
| TY21.6 | − |
| TY21.12 | +/− |

In addition to VCAM-1, α4β1 integrin mediates cell binding to the CS-1 domain of FN. Some antibodies against α4 integrin inhibit FN binding, as is the case for L25, TY21.6 and TY21.12; all three antibodies were as effective as HP2/1. This assay was performed as described in Pulido et al., (1991) supra. The results are summarized in Table 11.

TABLE 11

| | Jurkat Binding to Fibronectin: | | | | | |
|---|---|---|---|---|---|---|
| Plate coating | BSA | FN | FN | FN | FN | FN |
| Jurkat treatment | none | none | HP2/1 | 21.6 | 21.12 | L25 |
| % input bound | 2 ± 1 | 77 ± 6 | 42 ± 7 | 43 ± 6 | 34 ± 2 | 32 ± 1 |
| (% inhibition) | — | — | (47) | (45) | (55) | (60) |

It will be useful to examine the efficacy of the anti-α4 antibodies in animal models of human disease. Thus, the ability of the antibodies to cross react with peripheral blood lymphocytes from a number of different species were compared (FACS analysis, as described above, using whole blood lymphocytes). The results of the comparisons are shown in Table 12.

TABLE 12

| Antibody | Human | Rhesus | Cynomolgus | Dog | Rabbit | Guinea Pig | Rat | Gerbil |
|---|---|---|---|---|---|---|---|---|
| HP2/1 | +++ | +++ | +++ | +++ | ++ | +++ | +++ | — |
| L25 | +++ | +++ | +++ | +++ | +++ | +++ | +++ | — |
| TY21.6 | +++ | +++ | +++ | ++ | — | +++ | — | — |
| TY21 | +++ | +++ | +++ | ++ | — | +++ | — | — |

Although the invention has been described with reference to the presently preferred embodiments, it should be understood that various modifications can be made without departing from the spirit of the invention. Accordingly, the invention is limited only by the following claims.

I claim:

1. A method for inhibiting or ameliorating brain inflammation comprising administering a reagent capable of inhibiting binding of leukocyte cell surface receptor VLA-4 to brain endothelial cell adhesion molecule VCAM-1.

2. In a method for treating chronic inflammatory brain disease, the improvement comprising administering a therapeutically effective dosage of a reagent that inhibits leukocyte cell surface receptor VLA-4 from binding to a brain endothelial adhesion molecule VCAM-1.

3. The method of claim 1 or 2, wherein the brain inflammation is associated with multiple sclerosis, experimental autoimmune encephalomyelitis or meningitis.

4. The method of claim 3, wherein the reagent is selected from the group consisting of an antibody, an antibody fragment thereof and a peptide.

5. The composition of claim 3, wherein the reagent is directed against leukocyte cell surface receptor VLA-4.

6. The method of claim 5, wherein the reagent is directed against the α4 subunit of leukocyte cell surface receptor VLA-4.

7. The method of claim 5, wherein the reagent binds to the α4 subunit of VLA-4 only in association with the β1 subunit.

8. The method of claim 4, wherein the reagent is a monoclonal antibody.

9. A method of treating a pathology associated with an accumulation of leukocytes in the central nervous system of a subject comprising administering to the subject an effective amount of the pharmaceutical composition comprising a reagent chosen from the group consisting of an antibody, an antibody fragment thereof and a peptide, which reagent is capable of inhibiting binding of leukocyte cell surface receptor VLA-4 to brain endothelial cell adhesion molecule VCAM-1, and a pharmaceutically-acceptable carrier, thereby alleviating the pathology associated with an accumulation of leukocytes in the central nervous system of the subject.

10. A method of treating a pathology associated with an accumulation of leukocytes in the central nervous system of a subject comprising administering to the subject an effective amount of the pharmaceutical composition for inhibiting or ameliorating multiple sclerosis, experimental autoimmune encephalomyelitis or meningitis, comprised of at least one reagent that is an antibody, a fragment thereof, or a peptide, which reagent inhibits binding of leukocyte cell surface receptor VLA-4 to brain endothelial adhesion molecule VCAM-1, and a pharmaceutically-acceptable carrier, thereby treating the pathology associated with an accumulation of leukocytes in the central nervous system of the subject.

11. A method for treating multiple sclerosis, comprising administering to a subject a therapeutically effective amount of a pharmaceutical composition comprising a reagent chosen from the group consisting of comprising an antibody, an antibody fragment thereof and a peptide, which reagent is capable of inhibiting binding of leukocyte cell surface receptor VLA-4 to brain endothelial cell adhesion molecule VCAM-1, and a pharmaceutically-acceptable carrier, thereby alleviating the pathological condition associated with multiple sclerosis.

12. The method of claim 11, wherein the pathological condition is impaired nerve condition.

13. The method of claim 11, wherein the pathological condition is paralysis.

* * * * *